US007884123B2

(12) United States Patent
Carry et al.

(10) Patent No.: US 7,884,123 B2
(45) Date of Patent: Feb. 8, 2011

(54) SUBSTITUTED THIENO[2,3-C]PYRAZOLES, PROCESS FOR PREPARING THEM, COMPOSITIONS CONTAINING THEM, AND USE THEREOF

(75) Inventors: Jean-Christophe Carry, Saint Maur des Fossés (FR); Gilles Doerflinger, Les Ulis (FR); Antony Bigot, Massy (FR); Dominique Barbalat-Damour, Orly (FR); François Clerc, Antony (FR); Arielle Genevois-Borella, Thiais (FR); Baptiste Ronan, Clamart (FR); Hervé Minoux, Thiais (FR); Claude Barberis, Hillsborough, NJ (US); Yves Janin, Paris (FR)

(73) Assignee: Aventis Pharma S.A., Antony (FR)

( * ) Notice: Subject to any disclaimer, the term of this patent is extended or adjusted under 35 U.S.C. 154(b) by 693 days.

(21) Appl. No.: 11/752,612

(22) Filed: May 23, 2007

(65) Prior Publication Data
US 2008/0058402 A1   Mar. 6, 2008

Related U.S. Application Data

(63) Continuation of application No. PCT/FR2005/002933, filed on Nov. 25, 2005.

(30) Foreign Application Priority Data
Nov. 29, 2004 (FR) .................................. 04 12644

(51) Int. Cl.
*A61K 31/4162* (2006.01)
*C07D 487/04* (2006.01)
(52) U.S. Cl. ..................... 514/407; 514/406; 548/360.5
(58) Field of Classification Search ........................ None
See application file for complete search history.

(56) References Cited

U.S. PATENT DOCUMENTS

2005/0026984 A1    2/2005   Bigot et al.
2005/0261339 A1    11/2005  Ohi et al.

FOREIGN PATENT DOCUMENTS

| EP | 1 510 516 A1 | 3/2005 |
|---|---|---|
| WO | WO 03/101968 A1 | 12/2003 |
| WO | WO 2004/007504 A1 | 1/2004 |
| WO | WO 2004/013146 A1 | 2/2004 |

OTHER PUBLICATIONS

Albericio et al, An Improved Synthesis of N-[(9-hydroxymethyl)-2-fluorenyl]succinamic Acid (HMFS), A Versatile Handle for the Solid-Phase Synthesis of Biomolecules, Synthetic Comm., 2001 (31) 2 pp. 225-232.
Asahara et al, Tie2 Receptor Ligands, Angiopoietin-1 and Angiopoietin-2, Modulate VEGF-Induced Postnatal Neovascularization, Circ. Res., 1998 (83) pp. 233-240.
Bischoff et al, A homologue of *Drosophila* aurora kinase is oncogenic and amplified in human colorectal cancers, EMBO; 1998 (17) 11 pp. 3052-3065.
Cary et al, Stimulation of cell migration by overexpression of focal adhesion kinase and its association with Src and Fyn, Journal of Cell Science, 1996 (109), pp. 1787-1794.
Chen et al, Association of focal adhesion kinase with its potential substrate phosphatidylinositol 3-kinase, Proc. Natl. Acad. Sci. USA, 1994 (91), pp. 10148-10152.
Daidone et al, Synthesis, Crystallographic Studies and Biological Evaluation of some 2-Substituted 3-Indazolyl-4(3H)-Quinazolinones and 3-Indazolyl-4(3H)-Benzotriazinones, Heterocycles 1996 (43) 11 pp. 2385-2396.
Davies et al, Inhibitor Binding to Active and Inactive CDK2: The Crystal Structure of CDK2-Cyclin A/Indirubin-5-Sulphonate, Structure, 2001 (9) pp. 389-397.
Davis et al, Isolation of Angiopoietin-1, a Ligand for the TIE2 Receptor, by Secretion-Trap Expression Cloning, Cell, 1996 (87) pp. 1161-1169.
Dumont et al, Dominant-negative and targeted null mutations in the endothelial receptor tyrosine kinase, tek, reveal a critical role in vasculogenesis of the embryo, Genes Dev., 1994 (8) pp. 1897-1909.
Klapars et al, A General and Efficient Copper Catalyst for the Amidation of Aryl Halides and the N-Arylation of Nitrogen Heterocycles, JACS, 2001 (123) pp. 7727-7729.
Klapars et al, A General and Efficient Copper Catalyst for the Amidation of Aryl Halides, JACS, 2002 (124) 25 pp. 7421-7428.
Kornberg et al, Cell Adhesion or Integrin Clustering Increases Phosphorylation of a Focal Adhesion-associated Tyrosine Kinase, J. Biol. Chem., 1992 (267) 33, pp. 23439-23442.
Lee et al, Anti-Vascular Endothelial Growth Factor Treatment Augments Tumor Radiation Response under Normoxic or Hypoxic Conditions 1, Cancer Research, 2000 (60) 19 pp. 5565-5570.
Lin et al, Antiangiogenic gene therapy targeting the endothelium-specific receptor tyrosine kinase Tie2, PNAS, 1998 (95) pp. 8829-8834.

(Continued)

*Primary Examiner*—Kamal A Saeed
(74) *Attorney, Agent, or Firm*—Kelly L. Bender; R. Brian McCaslin

(57) ABSTRACT

Compounds of formula (I),

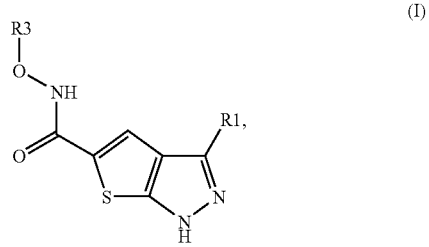

wherein R1 and R3 have the meanings given in the description, said compounds being in all isomeric forms; and salts thereof; processes for the preparation of the compounds and intermediates; compositions containing them, and the use thereof as medicaments, particularly as anti-cancer agents.

26 Claims, No Drawings

OTHER PUBLICATIONS

Lin et al, Inhibition of Tumor Angiogenesis Using a Soluble Receptor Establishes a Role for Tie2 in Pathologic Vascular Growth, J. Clin. Invest., 1997 (100) 8 pp. 2072-2078.

Ling et al, Malignant Astrocytoma Cell Attachment and Migration to Various Matrix Proteins Is Differentially Sensitive to Phosphoinositide 3-OH Kinase Inhibitors, J. Cell. Biochemistry, 1999 (73), pp. 533-544.

Maisonpierre et al, Angiopoietin-2, a Natural Antagonist for Tie2 That Disrupts in vivo Angiogenesis, Science, 1997 (277) pp. 55-60.

Maung et al, Requirement for focal adhesion kinase in tumor cell adhesion, Oncogene,1999 (18), pp. 6824-6828.

Millauer et al, Dominant-Negative Inhibition of Flk-1 Suppresses the Growth of Many Tumor Types in Vivo, Cancer Research, 1996 (56) pp. 1615-1620.

Oktay et al, Integrin-mediated Activation of Focal Adhesion Kinase Is Required for Signaling to Jun NH2-terminal Kinase and Progression through the G1 Phase of the Cell Cycle, J. Cell. Biol., 1999 (145) 7 pp. 1461-1469.

Owens et al, Overexpression of the Focal Adhesion Kinase (p125 FAK) in Invasive Human Tumors 1, Cancer Research, 1995 (55), pp. 2752-2755.

Procter et al, Beta-Lactams from Tetrahydro-1,2-oxazine-3,6-diones, and a Labelling Study of the Product Stereochemistry, Tetrahedron 1995 (51) 47 pp. 12837-12842.

Richardson et al, A mechanism for regulation of the adhesion-associated protein tyrosine kinase pp125 FAK, Nature, 1996 (380), pp. 538-540.

Roy et al, Early Development of Cyclin Dependent Kinase Modulators, Current Pharmaceutical Design, 2001 (7) pp. 1669-1687.

Schaller et al, Autophosphorylation of the Focal Adhesion Kinase, pp125 FAK, Directs SH2-Dependent Binding of pp60src, Mol. Cell. Biol., 1994 (14), pp. 1680-1688.

Schlaepfer et al, Focal Adhesion Kinase Overexpression Enhances Ras-dependent Integrin Signaling to ERK2/Mitogen-activated Protein Kinase through Interactions with and Activation of c-Src, J. Biol. Chem., 1997 (272) 20, pp. 13189-13195.

Schlaepfer et al, Integrin-mediated signal transduction linked to Ras pathway by GRB2 binding to focal adhesion kinase, Nature, 1994 (372) 22, pp. 786-791.

Schlaepfer et al, Signaling through focal adhesion kinase, Prog. Biophy. Mol. Biol., 1999 (71), pp. 435-478.

Sieg et al, Required role of focal adhesion kinase (FAK) for integrin-stimulated cell migration, J. Cell Science, 1999 (112), pp. 2677-2691.

Stille, The Palladium-Catalyzed Cross-Coupling Reactions of Organotin Reagents with Organic Electrophiles, Angew. Chem. Innt. Ed. Engl., 1986 (25) pp. 508-524.

Strawn et.al, Flk-1 as a Target for Tumor Growth Inhibition, Cancer Research, 1996 (56) pp. 3540-3545.

Suri et al, Requisite Role of Angiopoietin-1, a Ligand for the TIE2 Receptor, during Embryonic Angiogenesis, Cell, 1996 (87) pp. 1171-1180.

Suzuki, Synmthetic studies via the cross-coupling reaction of organoboron derivatives with organic halides, Pure & Appl. Chem., 1991 (63) 3 pp. 419-422.

Toogood, Cyclin-Dependent Kinase Inhibitors for Treating Cancer, Med. Res. Rev., 2001 (21) 6 pp. 487-498.

Vuori et al, Induction of p130cas Signaling Complex Formation upon Integrin-Mediated Cell Adhesion: a Role for Src Family Kinases, Mol. Cell. Biol., 1996 (16) 6, pp. 2606-2613.

Wang et al, p125 focal adhesion kinase promotes malignant astrocytoma cell proliferation in vivo, J. Cell Sci., 2000 (113), pp. 4221-4230.

Weiner et al, Expression of focal adhesion kinase gene and Invasive cancer, Lancet., 1993 (342), pp. 1024-1025.

Xing et al, Direct Interaction of v-Src with the Focal Adhesion Kinase Mediated by the Src SH2 Domain, Mol. Cell. Biol., 1994 (5), pp. 413-421.

Xu et al, Attenuation of the Expression of the Focal Adhesion Kinase Induces Apoptosis in Tumor Cells, Cell Growth Diff., 1996 (7), pp. 413-418.

Zhao et al, Regulation of the Cell Cycle by Focal Adhesion Kinase, J. Cell. Biol., 1998 (143) 7, pp. 1997-2008.

SUBSTITUTED THIENO[2,3-C]PYRAZOLES, PROCESS FOR PREPARING THEM, COMPOSITIONS CONTAINING THEM, AND USE THEREOF

The present invention relates especially to substituted thieno[2,3-c]pyrazoles, to a process for preparing them, to compositions containing them and to their use as medicaments.

More particularly, and according to a first aspect, the invention relates to substituted thieno[2,3-c]pyrazoles that are useful as anticancer agents.

1H-Thieno[2,3-c]pyrazoles are known from WO 04/013 146 and WO 03/101 968. These products are presented as inhibitors of numerous protein kinases. However, the administration of such products to patients may induce considerable side effects, on account of their broad spectrum of action. Thus, the production of specific inhibitors of a selection of proteins, especially of kinases, is desired.

Against all expectation, it has been found that it is possible to obtain inhibitors of the kinase Aurora2 (Aurora A) and of certain other kinases that are useful in oncology, with substituted 1H-thieno[2,3-c]pyrazoles.

One subject of the present invention is thus products which are characterized in that they correspond to the general formula (I) below:

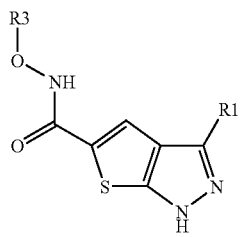

in which:
(i) R1 is independently selected from the group consisting of R2, NHCO(R2), —CH═CH—(R2), NH—R4 in which R2 is independently selected from the group consisting of —(C1-C24)alkyl, —(C3-C9)cycloalkyl, heterocycloalkyl, heterocycloalkylene, aryl, heteroaryl, arylalkyl, heteroarylalkyl;
(ii) R3 is independently selected from the group consisting of —(C1-C6)alkyl, —(C1-C6)alkylaryl, —(C1-C6)alkylheteroaryl, -aryl, -heteroaryl;
(iii) R4 represents aryl, heteroaryl, —(C3-C9)cycloalkyl, heterocycloalkyl, the radicals R2, R3 and R4 being optionally substituted with one or more radicals, which may be identical or different, chosen from halogen atoms and the following radicals: hydroxyl, alkoxy, cycloalkyl, NH2, NHAlk, N(Alk)2, alkyl, hydroxyalkyl, heterocycloalkyl and phenyl, which is itself optionally substituted with one or more radicals, which may be identical or different, chosen from halogen atoms and hydroxyl, NH2, alkoxy, alkyl and hydroxyalkyl radicals;

with the proviso that when R3 is —(C1-C6)alkyl, then R1 is not: aryl, heteroaryl or —CH═CH—(R2), in which R2 is selected from the group consisting of aryl and heteroaryl, said products of formula (I) being in any possible racemic, enantiomeric or diastereoisomeric isomer form, and also the addition salts with mineral and organic acids or with mineral and organic bases of said products of formula (I).

These products correspond to the general formula (I) below:

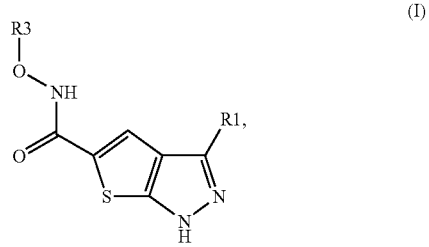

in which:
(i) R1 is independently selected from the group consisting of R2, NHCO(R2), —CH═CH—(R2), in which R2 is independently selected from the group consisting of —(C1-C24)alkyl, —(C3-C9)cycloalkyl, heterocycloalkyl, heterocycloalkylene, aryl, heteroaryl, arylalkyl, heteroarylalkyl;
(ii) R3 is independently selected from the group consisting of —(C1-C6)alkyl, —(C1-C6)alkylaryl, —(C1-C6)alkylheteroaryl, -aryl, -heteroaryl;

with the proviso that when R3 is —(C1-C6)alkyl, then R1 is not: aryl, heteroaryl or —CH═CH—(R2), in which R2 is selected from the group consisting of aryl and heteroaryl.

A subject of the present invention is thus a product of formula (I) as defined above, characterized in that R1 is chosen from aryl, heteroaryl, NHCO(R2) and NH—R4, with R2 being independently selected from the group consisting of —(C1-C24)alkyl, —(C3-C9)cycloalkyl, heterocycloalkyl, heterocycloalkylene, aryl, heteroaryl, arylalkyl, heteroarylalkyl and R4 represents aryl, heteroaryl, —(C3-C9)cycloalkyl and heterocycloalkyl.

A subject of the present invention is thus a product of formula (I) as defined above, characterized in that R1 represents NH—R4, with R4 representing aryl, heteroaryl, —(C3-C9)cycloalkyl and heterocycloalkyl.

In the products of formula (I) and in the text hereinbelow:
the term "alkyl radical" denotes linear and branched radicals containing up to 12 carbon atoms, for instance methyl, ethyl, propyl, isopropyl, butyl, isobutyl, sec-butyl, tert-butyl, pentyl, isopentyl, hexyl, isohexyl, heptyl, octyl, nonyl and decyl radicals, and also the linear or branched positional isomers thereof;
the term "halogen atom" denotes chlorine, bromine, iodine or fluorine atoms and preferably the chlorine, bromine or fluorine atom;
the term "cycloalkyl radical" denotes a saturated carbocyclic radical containing 3 to 10 carbon atoms and thus especially denotes cyclopropyl, cyclobutyl, cyclopentyl and cyclohexyl radicals and most particularly cyclopentyl and cyclohexyl radicals;
the term "heterocycloalkyl radical" thus denotes a monocyclic or bicyclic carbocyclic radical interrupted with one or more heteroatoms, which may be identical or different, chosen from oxygen, nitrogen and sulfur atoms: examples that may be mentioned include the morpholinyl, thiomorpholinyl, aziridyl, azetidyl, piperazinyl, piperidyl, homopiperazinyl, pyrrolidinyl, imidazolidinyl, pyrazolidinyl, tetrahydrofuryl, tetrahydrothienyl, hexahydropyran and oxodihydropyridazinyl radicals, all these radicals being optionally substituted;

the terms "aryl" and "heteroaryl" denote unsaturated or partially unsaturated carbocyclic or, respectively, heterocyclic, monocyclic or bicyclic radicals, which are up to 12-membered, possibly containing a —C(O) ring member, the heterocyclic radicals containing one or more identical or different heteroatoms chosen from O, N and S, with N being optionally substituted, where appropriate;

the term "aryl radical" thus denotes 4- to 12-membered monocyclic or bicyclic radicals, for instance phenyl, naphthyl, biphenyl, indenyl, fluorenyl and anthracenyl radicals, more particularly phenyl and naphthyl radicals and even more particularly the phenyl radical. It may be noted that a carbocyclic radical containing a —C(O) ring member is, for example, the tetralone radical;

the term "heteroaryl radical" thus denotes 4- to 12-membered monocyclic or bicyclic radicals: monocyclic heteroaryl radicals such as, for example, dioxolane, dioxane, dithiolane, thiooxolane, thiooxane, thienyl such as 2-thienyl and 3-thienyl, furyl such as 2-furyl or 3-furyl, pyranyl, pyrrolyl, pyrrolinyl, pyrazolinyl, imidazolyl, pyrazolyl, pyridyl such as 2-pyridyl, 3-pyridyl and 4-pyridyl, pyrazinyl, pyrimidinyl, pyridazinyl, oxazolyl, thiazolyl, isothiazolyl, diazolyl, thiadiazolyl, thiatriazolyl, oxadiazolyl, isoxazolyl such as 3- or 4-isoxazolyl, furazanyl and free or salified tetrazolyl radicals, these radicals being optionally substituted, among which more particularly thienyl such as 2-thienyl and 3-thienyl, furyl such as 2-furyl, pyrrolyl, pyrrolinyl, pyrazolinyl, imidazolyl, pyrazolyl, oxazolyl, isoxazolyl, pyridyl and pyridazinyl radicals, all these radicals being optionally substituted; bicyclic heteroaryl radicals such as, for example, benzothienyl such as 3-benzothienyl, benzothiazolyl, quinolyl, isoquinolyl, dihydroquinolyl, quinolone, tetralone, adamantyl, benzofuryl, isobenzofuryl, dihydrobenzofuran, ethylenedioxyphenyl, thianthrenyl, benzopyrrolyl, benzimidazolyl, benzoxazolyl, thionaphthyl, indolyl, azaindolyl, indazolyl, purinyl, thienopyrazolyl, tetrahydroindazolyl, tetrahydrocyclopentapyrazolyl, dihydrofuropyrazolyl, tetrahydropyrrolopyrazolyl, oxotetrahydropyrrolopyrazolyl, tetrahydropyranopyrazolyl, tetrahydropyridinopyrazolyl or oxodihydropyridinopyrazolyl radicals, all these radicals being optionally substituted.

The carboxyl radical(s) of the products of formula (I) may be salified or esterified with various groups known to those skilled in the art, among which mention may be made, for example, of:

among the salification compounds, mineral bases such as, for example, one equivalent of sodium, potassium, lithium, calcium, magnesium or ammonium, or organic bases such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine or N-methylglucamine, among the esterification compounds, alkyl radicals to form alkoxycarbonyl groups such as, for example, methoxycarbonyl, ethoxycarbonyl, tert-butoxycarbonyl or benzyloxycarbonyl, these alkyl radicals possibly being substituted with radicals chosen, for example, from halogen atoms and hydroxyl, alkoxy, acyl, acyloxy, alkylthio, amino or aryl radicals, for instance from chloromethyl, hydroxypropyl, methoxymethyl, propionyloxymethyl, methylthiomethyl, dimethylaminoethyl, benzyl and phenethyl groups.

The addition salts with mineral or organic acids of the products of formula (I) may be, for example, the salts formed with hydrochloric acid, hydrobromic acid, hydriodic acid, nitric acid, sulfuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, alkylmonosulfonic acids, for instance methanesulfonic acid, ethanesulfonic acid or propanesulfonic acid, alkyldisulfonic acids, for instance methanedisulfonic acid or α,β-ethanedisulfonic acid, arylmonosulfonic acids such as benzenesulfonic acid and aryldisulfonic acids.

It may be recalled that stereoisomerism may be defined in its broad sense as the isomerism of compounds having the same structural formulae but whose various groups are arranged differently in space, especially such as in monosubstituted cyclohexanes whose substituent may be in an axial or equatorial position, and the various possible rotational conformations of ethane derivatives. However, there is another type of stereoisomerism, due to the various spatial arrangements of fixed substituents, either on double bonds or on rings, which is often referred to as geometrical isomerism or cis-trans isomerism. The term "stereoisomers" is used in the present patent application in its broadest sense and thus concerns all of the compounds indicated above.

The aryl and heteroaryl radicals especially represent phenyl, pyridyl, indolyl, benzimidazolyl, pyrazolyl and pyrrolyl.

A preferred R1 may be chosen from aryl; heteroaryl; —CH═CH—(R2), in which R2 is chosen from aryl and heteroaryl; and NHCO(R2).

A preferred R3 is advantageously chosen from aryl and heteroaryl, preferably from phenyl, pyridyl, indolyl, benzimidazolyl, pyrazolyl and pyrrolyl.

Illustrative products of the invention according to its first aspect may be chosen from:

3-(1H-indol-2-yl)-1H-thieno[2,3-c]pyrazole-5-(N-phenoxycarboxamide), 3-((E)-styryl)-1H-thieno[2,3-c]pyrazole-5-(N-phenoxycarboxamide), and 3-[(thiophene-2-carbonyl)amino]-1H-thieno[2,3-c]pyrazole-5-(N-phenoxycarboxamide).

The products in accordance with the invention may be in achiral form, or racemic form, or in a form enriched in one stereoisomer, or enriched in one enantiomer; and are optionally salified.

According to a second aspect, a subject of the invention is a process for preparing the products according to its first aspect.

In particular, the invention relates to a process for preparing a product of general formula (I) below:

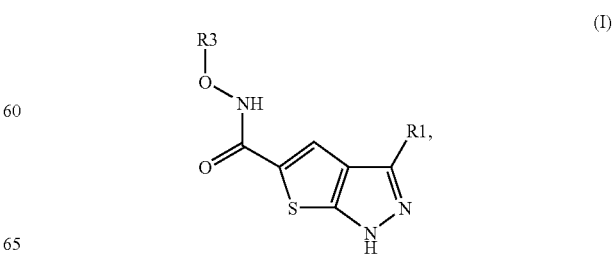

(I)

in which R1 is NHCO(R2), and in which R2 and R3 are as defined above, said product of general formula (I) being obtained by:

(i) coupling between (i-a) an amine of general formula (X) below:

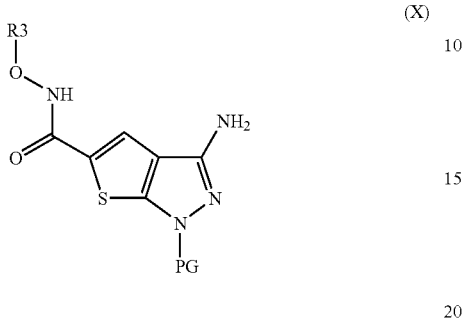

in which R3 is as defined above, and in which PG is a protecting group for the free endocyclic NH function of the thieno[2,3-c]pyrazole nucleus, and (i-b) a carboxylic acid R2-COOH in the presence of a coupling agent or a carboxylic acid derivative such as an acid chloride or an anhydride, in the presence of a base such as a tertiary amine or an alkali metal carbonate; and then (ii) cleavage of PG.

According to one preferred embodiment, the amine of general formula (X) is obtained by protecting the NH function of the pyrazole nucleus of a product of general formula (IX):

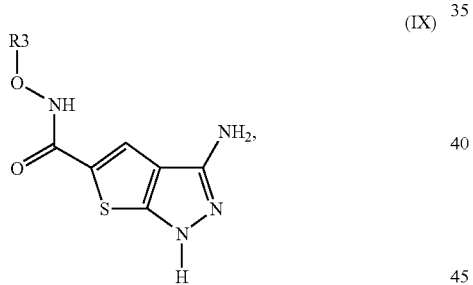

in which R3 is as defined above, the product of general formula (IX) being obtained by reaction between:

(i) R3ONH$_2$, in the presence of a trialkylaluminum, for example trimethylaluminum, and (ii) a product of general formula (XIV):

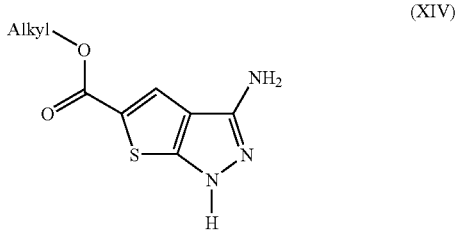

in which alkyl is (C1-C6)alkyl.

According to its second aspect, the invention also relates to a process for preparing a product of general formula (Ia) or (IIIa) below:

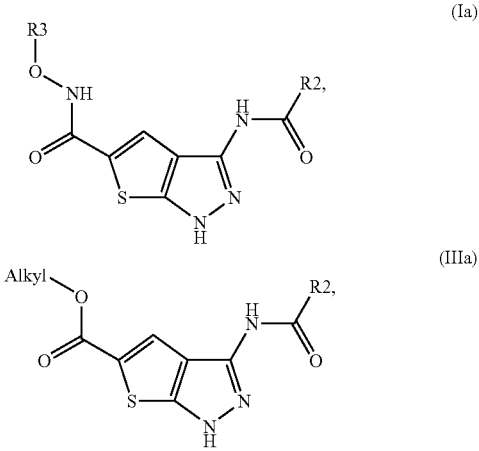

in which R2 and R3 are as defined above and alkyl is (C1-C6)alkyl, said product of general formula (Ia) or (IIIa) being obtained by means of the following steps:

(i) coupling between (i-a) a product of general formula (V) or (IIa) below:

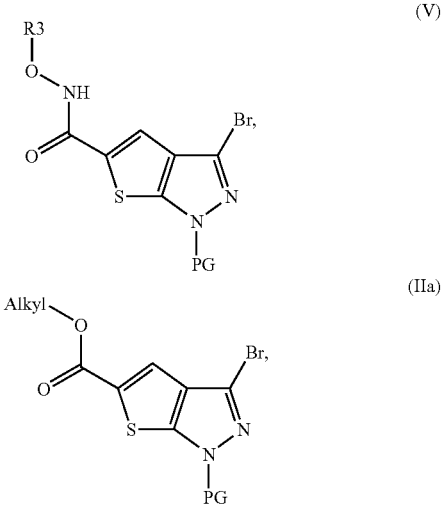

in which R3 and alkyl are as defined above, and in which PG is a protecting group for the free endocyclic NH function of the thieno[2,3-c]pyrazole nucleus, and (i-b) a product of general formula (R2)CONH$_2$, in the presence of:

a catalyst such as copper(I) iodide, an amine such as trans-1,2-diaminocyclohexane, trans-1,2-bis(methylamino)cyclohexane or, preferably, N,N'-dimethyl-1,2-diaminoethane, and a base such as tripotassium phosphate or cesium carbonate, and (ii) cleavage of PG.

According to its second aspect, the invention also relates to a process for preparing a product of general formula (IIa) below:

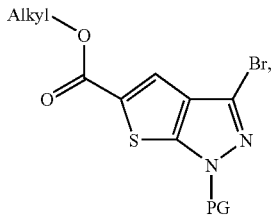

(II)

in which alkyl and PG are as defined above, comprising a step in which a product of general formula (VIIIa):

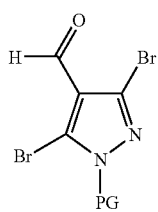

(VIIIa)

is cyclized with an alkyl mercaptoacetate alkyl-OCO—CH$_2$—SH, in the presence of a base such as sodium carbonate.

The product of general formula (VIIIa) is advantageously obtained by (i) formylation of 3,4,5-tribromopyrazole to give 3,5-dibromo-4-formylpyrazole (VIII), followed by (ii) protection of the endocyclic amine function of (VIII).

A preferred protection reaction may be performed in the presence of ethyl vinyl ether and of a catalytic amount of an acid such as hydrochloric acid.

A subject of the present invention is also, as medicaments, the products of formula (I) as defined above, and also the addition salts with pharmaceutically acceptable mineral and organic acids or with pharmaceutically acceptable mineral and organic bases of said products of formula (I).

According to a third aspect, the invention relates to a pharmaceutical composition comprising a product according to its first aspect, in combination with a pharmaceutically acceptable excipient.

According to a fourth aspect, a subject of the invention is the use of a product according to its first aspect, as an inhibitor of a protein kinase, preferably chosen from Aurora2, CDK1, CDK2, CDK4, FAK, KDR, PLK1 and Tie2.

Thus, a subject of the invention is the use of a product according to its first aspect, as an inhibitor of a protein kinase, preferably chosen from Aurora2, CDK1, CDK2, CDK4, FAK, KDR and Tie2.

A particularly preferred kinase is Aurora2.

A particularly preferred kinase is PLK1.

According to a fifth aspect, a subject of the invention is the use of a product according to its first aspect, for the manufacture of a medicament that is useful for treating a pathological condition, in particular cancer.

The compounds of formula (I) may be prepared from the compounds of general formula (II) according to the following general synthetic scheme:

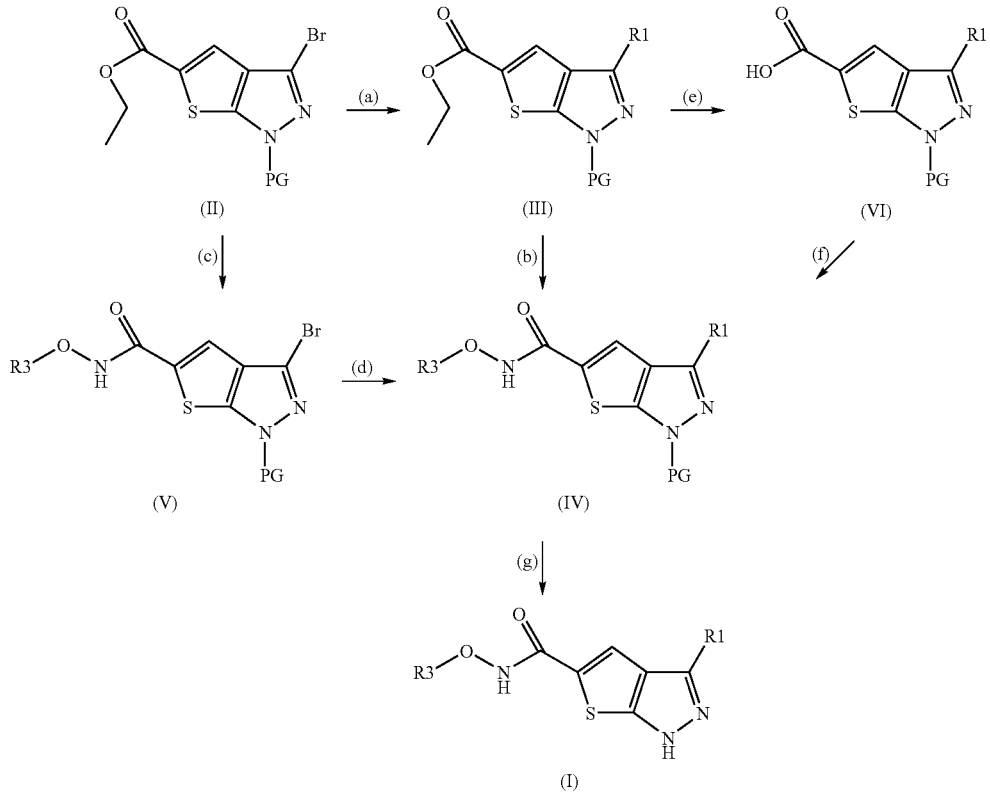

Reactions (a) and (d) may be performed in the presence of a derivative of a boronic acid of the type R1B(OR')$_2$ in which R1 has the same meaning as above, a palladium (0) derivative such as tetrakis(triphenylphosphine)palladium (0) or 1,1'-bis(diphenylphosphino)ferrocene-dichloropalladium (II), a base such as sodium carbonate or cesium carbonate in an inert solvent such as a mixture of toluene, an alcohol (preferably ethanol) and water, or such as dimethylformamide, at a temperature of between 20° C. and the boiling point of the reaction medium, according to the general methods described by A. Suzuki, Pure Appl. Chem., 1991, 63, 419, or alternatively in the presence of a derivative of the type Sn(R1)$_4$ in which R1 has the same meaning as above, a palladium derivative such as dichlorobis(triphenylphosphine)palladium (II) in an inert solvent such as dimethylformamide or dioxane, at a temperature of between 20° C. and the boiling point of the reaction medium, according to the general methods described by J. Stille, Angew. Chem. Int. Ed., 1986, 25, 508. Alternatively, when R1 represents NHCO(R2) in which R2 has the same meaning as above, this reaction may be performed in the presence of an amide of the type (R2)CONH$_2$, copper(I) iodide, an amine such as trans-1,2-diaminocyclohexane, trans-1,2-bis(methylamino)cyclohexane or—and this is one of the aspects of the invention —N,N'-dimethyl-1,2-diaminoethane, and of a base such as tripotassium phosphate or cesium carbonate, in an inert solvent such as dioxane, at a temperature of between 20° C. and the boiling point of the reaction medium, according to the general methods described by S. L. Buchwald et al., J. Am. Chem. Soc., 2002, 124, 7421; J. Am. Chem. Soc., 2001, 123, 7727.

Alternatively, when R1 represents NHR4 in which R4 has the same meaning as above, reactions (a) and (d) may be performed in the presence of an amine of the type R4NH2, of copper(I) iodide and of a base, for instance cesium carbonate, in an inert solvent, for instance dioxane, at a temperature of between 20° C. and the boiling point of the reaction medium, according to the usual methods known to those skilled in the art.

Alternatively, when R1 represents NHR4 in which R4 has the same meaning as above, reactions (a) and (d) may also be performed according to the usual aromatic nucleophilic substitution (ArNS) methods.

Reactions (b) and (c) may be performed in the presence of a derivative of the type R3ONH$_2$ in which R3 has the same meaning as above, and of trimethylaluminum, in a solvent such as toluene, at a temperature of between 0° C. and the boiling point of the reaction medium.

Reaction (e) is generally performed according to the usual methods that do not affect the rest of the molecule, especially by applying the methods described by T. W. Greene and P. G. M. Wuts, Protective Groups in Organic Synthesis (2$^{nd}$ edition), A. Wiley—Interscience Publication (1991), or by McOmie, Protective Groups in Organic Chemistry, Plenum Press (1973) or by Bradford P. Mundy and Michael G. Ellerd, Name Reactions and Reagents in Organic Synthesis, A. Wiley—Interscience Publication (1988). Reaction (e) may be performed, for example, in basic medium, in the presence of potassium hydroxide or sodium hydroxide, in an inert solvent, such as a mixture of tetrahydrofuran, water and an alcohol (preferably ethanol or methanol), or alternatively of an alcohol alone (preferably ethanol or methanol), at a temperature of between 20° C. and the boiling point of the reaction medium, preferably at the reflux temperature of the reaction medium.

Reaction (f) is preferably performed in the presence of a derivative of the type R3ONH$_2$ in which R3 has the same meaning as above and of an activating agent of the type such as O-(1H-benzotriazol-1-yl)-N,N,N',N'-tetramethyluronium tetrafluoroborate (TBTU), in the presence of a base (for example triethylamine or diisopropylethylamine), in an inert solvent (for example acetonitrile or dimethylformamide), at a temperature of between 0° C. and the boiling point of the medium, or according to the well-known coupling methods of peptide chemistry (M. Bodanszky et al., Principles of Peptide Synthesis, Springer-Verlag, New York, N.Y., 1984, 9-58) or methods for formation of an amide. Alternatively, reaction (f) may generally be performed according to the usual methods that do not affect the rest of the molecule, especially by applying the methods described by Bradford P. Mundy and Michael G. Ellerd, Name Reactions and Reagents in Organic Synthesis, A. Wiley—Interscience Publication (1988). For example, reaction (f) may be performed under an inert atmosphere (for example under nitrogen or under argon) in the presence of oxalyl chloride, in an inert solvent such as dichloromethane, at a temperature of between 20° C. and the boiling point of the reaction medium, preferably at a temperature in the region of 20° C., or alternatively in the presence of sulfinyl chloride, in an inert solvent such as chloroform, at a temperature of between 20° C. and the boiling point of the reaction medium, preferably at the reflux temperature of the reaction medium, followed by a reaction in the presence of a derivative of R3ONH$_2$ type in which R3 has the same meaning as above and of a base such as triethylamine or pyridine, in an inert solvent such as dimethylformamide, at a temperature of between 20° C. and the boiling point of the reaction medium.

The deprotection reaction (g) may be performed in the presence of a mineral acid such as hydrochloric acid, in a solvent such as tetrahydrofuran or water, at a temperature of between 20° C. and the boiling point of the reaction medium.

The compounds of general formula (II) may be prepared from 3,4,5-tribromopyrazole, according to the following general synthetic scheme:

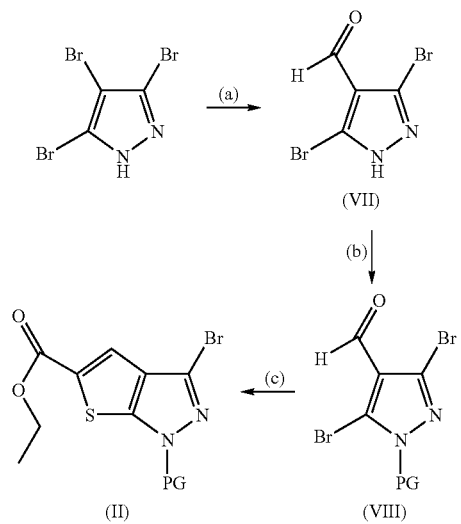

Reaction (a) may be performed in the presence of an organolithium reagent such as n-butyllithium, in the presence of dimethylformamide, in an inert solvent such as diethyl ether or tetrahydrofuran, at a temperature of between −78° C. and room temperature.

The protection reaction (b) may be performed in the presence of ethyl vinyl ether, in the presence of a catalytic amount of an acid such as hydrochloric acid, in an inert solvent such as toluene, at a temperature of between 20° C. and the boiling point of the reaction medium, or according to the well-known methods for protecting an amine function (T. W. Greene et al. in Protective Groups in Organic Synthesis, third edition, 1999, Wiley-Interscience).

Reaction (c) may be performed in the presence of ethyl mercaptoacetate, in the presence of a base such as sodium carbonate, in an inert solvent such as an alcohol (preferably ethanol), at a temperature of between 20° C. and the boiling point of the reaction medium.

Alternatively, when R1 represents NHCO(R2) in which R2 has the same meaning as above, the compounds of formula (I) may be prepared from the compounds of general formula (IX), according to the following general synthetic scheme:

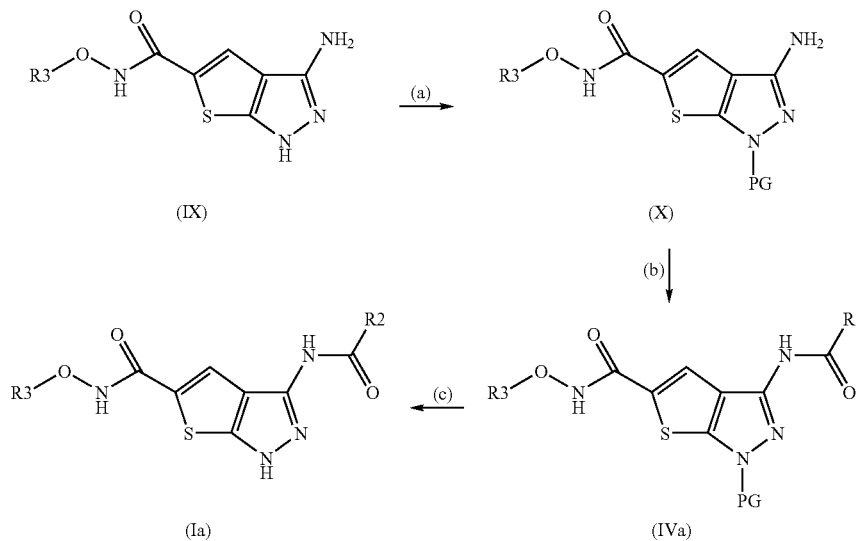

The protection reaction (a) may be performed (when P represents a tert-butyloxycarbonyl group) using di-tert-butyl dicarbonate in the presence of a base such as triethylamine or pyridine and optionally in the presence of N,N-dimethylaminopyridine, in an inert solvent (for example dichloromethane), at a temperature of between −10° C. and the boiling point of the reaction medium, or alternatively (when P represents a 1-ethoxyethyl group) in the presence of ethyl vinyl ether, in the presence of a catalytic amount of an acid such as hydrochloric acid, in an inert solvent such as toluene, at a temperature of between 20° C. and the boiling point of the reaction medium, or according to the well-known methods for protecting an amine function (T. W. Greene et al. in Protective Groups in Organic Synthesis, third edition, 1999, Wiley-Interscience).

Reaction (b) may be performed:

using an acid chloride (R2)C(O)Cl in which R2 has the same meaning as above, in the presence of a base, for instance triethylamine, pyridine, diisopropylethylamine, potassium carbonate or sodium carbonate, in an inert solvent (for example dimethylformamide or tetrahydrofuran) or in the organic base itself, at a temperature of between 0° C. and the boiling point of the reaction medium (G. Daidone et al., Heterocycles, 1996, 43(11), 2385);

using an anhydride ((R2)CO)$_2$O in which R2 has the same meaning as above, in an inert solvent (for example dimethylformamide, tetrahydrofuran or dichloromethane) or in the anhydride itself, at a temperature of between 0° C. and the boiling point of the reaction medium (F. Albericio, Synth. Commun., 2001, 31(2), 225, G. Procter, Tetrahedron, 1995, 51(47), 12837);

using an acid (R2)C(O)OH in which R2 has the same meaning as above, in the presence of an activating agent such as O-(7-azabenzotriazol-1-yl)-N,N,N',N'-tetramethyluronium hexafluorophosphate (HATU), in the presence of a base (for example pyridine, diisopropylethylamine or triethylamine), in an inert solvent (for example dimethylformamide), at a temperature of between 0° C. and the boiling point of the reaction medium, or according to the well-known coupling methods of peptide chemistry (M. Bodanszky et al., Principles of Peptide synthesis, Springer-Verlag, New York, N.Y., 1984, 9-58) or methods for the formation of an amide.

The deprotection reaction (c) may be performed (when P represents a tert-butyloxycarbonyl group) in the presence of iodotrimethylsilane, or in acidic medium (for example trifluoroacetic acid, or hydrochloric acid in a solvent such as dichloromethane or dioxane), or in basic medium (potassium carbonate in a solvent such as an alcohol (preferably methanol) at a temperature of between 0° C. and the boiling point of the reaction medium and optionally with microwave irradiation), or alternatively (when P represents a 1-ethoxyethyl group) in the presence of a mineral acid such as hydrochloric acid, in a solvent such as tetrahydrofuran or water, at a temperature of between 20° C. and the boiling point of the reaction medium, or alternatively according to the well-known methods for deprotecting an amine function (T. W. Greene at al. in Protective Groups in Organic Synthesis, third edition, 1999, Wiley-Interscience).

The compounds of general formula (IX) may be prepared from ethyl 3-amino-4-cyano-5-methylsulfanylthiophene-2-carboxylate, according to the following general synthetic scheme:

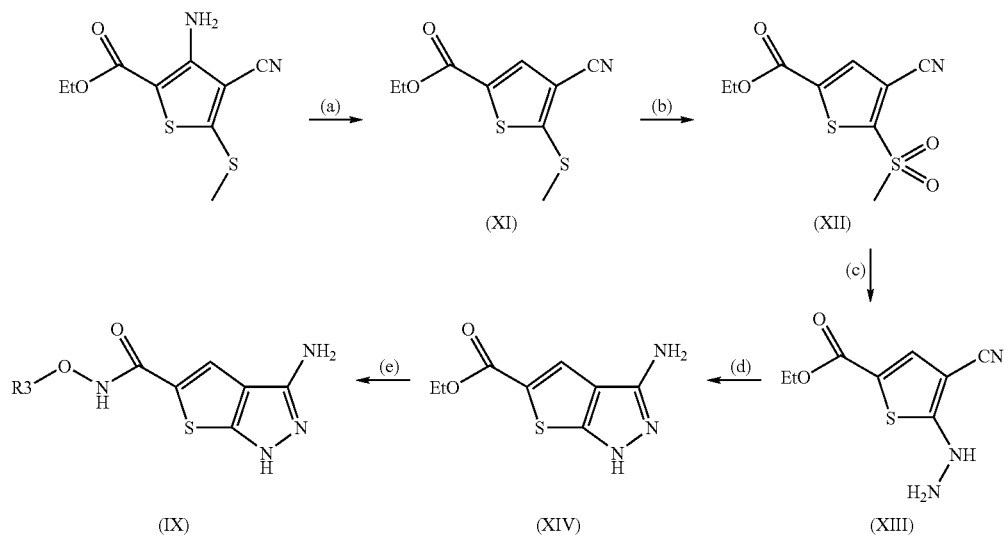

Reaction (a) may be performed in the presence of isopentyl nitrite, in an inert solvent such as dimethylformamide, at a temperature of between 20° C. and the boiling point of the reaction medium.

The oxidation reaction (b) may be performed in the presence of 3-chloroperoxybenzoic acid, in an inert solvent such as dichloromethane, at a temperature of between −20° C. and room temperature.

Reaction (c) may be performed in the presence of hydrazine, in an inert solvent such as an alcohol (preferably ethanol), at a temperature of between 20° C. and the boiling point of the reaction medium.

The cyclization reaction (d) may be performed in the presence of a mineral acid such as concentrated hydrochloric acid or concentrated sulfuric acid, in an inert solvent such as an alcohol (preferably ethanol), at a temperature of between 20° C. and the boiling point of the reaction medium.

Reaction (e) may be performed in the presence of a product of the type $R_3ONH_2$ in which R3 has the same meaning as above, and of trimethylaluminum, in a solvent such as toluene, at a temperature of between 0° C. and the boiling point of the reaction medium.

It is understood to those skilled in the art that, in order to perform the processes according to the invention described previously, it may be necessary to introduce protecting groups for the amine and carboxyl functions in order to avoid side reactions. These groups are those that can be removed without affecting the rest of the molecule. Examples of protecting groups for the amine function that may be mentioned include 1-ethoxyethyl, which may be regenerated in the presence of a mineral acid such as hydrochloric acid (in a solvent such as, for example, tetrahydrofuran or water), tert-butylcarbamate, which may be regenerated using iodotrimethylsilane or in acidic medium (for example trifluoroacetic acid, or hydrochloric acid in a solvent such as dichloromethane or dioxane), benzyl carbamate, which may be regenerated in the presence of hydrogen or in the presence of a mixture of a thiol (for example benzenethiol) and a Lewis acid (for example boron trifluoride etherate), acetyl, which may be regenerated in acidic medium (for example hydrochloric acid), benzoyl, which may be regenerated in acidic medium (for example hydrochloric acid), 2-trimethylsilanylethoxymethyl, which may be regenerated, for example, in the presence of tetrabutylammonium fluoride or in acidic medium (for example hydrochloric acid). Protecting groups for the carboxyl function that may be mentioned include esters (for example methoxymethyl ester, benzyl ester or methyl ester), which may be regenerated via the methods described in T. W. Greene et al. in Protective Groups in Organic Synthesis, third edition, 1999, Wiley-Interscience.

The compounds of formula (I) are isolated and may be purified via the usual known methods, for example by crystallization, chromatography or extraction.

The enantiomers and diastereoisomers of the compounds of formula (I) also form part of the invention.

The compounds of formula (I) comprising a basic residue may be optionally converted into addition salts with a mineral or organic acid via the action of such an acid in an organic solvent such as an alcohol, a ketone, an ether or a chlorinated solvent.

The compounds of formula (I) comprising an acid residue may be optionally converted into metal salts or into addition salts with nitrogenous bases according to the methods that are known per se. These salts may be obtained via the action of a metallic base (for example alkali metal or alkaline-earth metal base), ammonia, an amine or an amine salt on a compound of formula (I), in a solvent. The salt formed is separated out by the usual methods.

These salts also form part of the invention.

When a product according to the invention contains at least one free basic function, pharmaceutically acceptable salts may be prepared by reaction between said product and a mineral or organic acid. Pharmaceutically acceptable salts include the chlorides, nitrates, sulfates, hydrogen sulfates, pyrosulfates, bisulfates, sulfites, bisulfites, phosphates, monohydrogen phosphates, dihydrogen phosphates, metaphosphates, pyrophosphates, acetates, propionates, acrylates, 4-hydroxybutyrates, caprylates, caproates, decanoates, oxalates, malonates, succinates, glutarates, adipates, pimelates, maleates, fumarates, citrates, tartrates, lactates, phenylacetates, mandelates, sebacates, suberates, benzoates, phthalates, methanesulfonates, propanesulfonates, xylenesulfonates, salicylates, cinnamates, glutamates, aspartates, glucuronates and galacturonates.

When a product according to the invention contains at least one free acid function, pharmaceutically acceptable salts may be prepared by reaction between said product and a mineral or organic base. Pharmaceutically acceptable bases include hydroxides of cations of alkali metals or alkaline-earth metals such as Li, Na, K, Mg or Ca, and basic amine compounds such as ammonia, arginine, histidine, piperidine, morpholine, piperazine or triethylamine.

The invention is also described by the examples that follow, which are given as illustrations of the invention.

The LC/MS analyses were performed on an LCT model Micromass machine connected to an HP 1100 machine. The abundance of the products was measured using an HP G1315A diode array detector over a wavelength range of 200-600 nm and a Sedex 65 light-scattering detector. The mass spectra were acquired over a range from 180 to 800. The data were analyzed using the Micromass MassLynx software. Separation was performed on a Hypersil BDS C18, 3 μm (50×4.6 mm) column, eluting with a linear gradient of from 5% to 90% of acetonitrile containing 0.05% (v/v) of trifluoroacetic acid (TFA) in water containing 0.05% (v/v) of TFA, over 3.5 minutes at a flow rate of 1 ml/minute. The total analysis time, including the column re-equilibration period, is 7 minutes.

The preparative LC-MS purifications were generally performed using a Waters FractionsLynx system composed of a Waters model 600 gradient pump, a Waters model 515 regeneration pump, a Waters Reagent Manager dilution pump, a Waters model 2700 auto-injector, two Rheodyne model Lab-Pro valves, a Waters model 996 diode array detector, a Waters model ZMD mass spectrometer and a Gilson model 204 fraction collector. The system was controlled by Waters FractionLynx software. Separation was performed alternately on two Waters Symmetry columns (C$_{18}$, 5 μM, 19×50 mm, catalog reference 186000210), one column undergoing regeneration with a 95/5 (v/v) water/acetonitrile mixture containing 0.07% (v/v) of trifluoroacetic acid, while the other column was undergoing separation. The elution of the columns was performed using a linear gradient of from 5% to 95% of acetonitrile containing 0.07% (v/v) of trifluoroacetic acid in water containing 0.07% (v/v) of trifluoroacetic acid, at a flow rate of 10 ml/minute. At the separation column outlet, one-thousandth of the effluent was separated by an LC Packing Accurate, diluted with methyl alcohol at a flow rate of 0.5 ml/minute and sent to the detectors, in a proportion of 75% to the diode array detector and the remaining 25% to the mass spectrometer. The rest of the effluent (999/1000) was sent to the fraction collector where the flux was discarded if the mass of the expected product was not detected by the FractionLynx software. The molecular formulae of the expected products were supplied to the FractionLynx software, which triggered the collection of the product when the detected mass signal corresponded to the ion [M+H]$^+$ and/or to [M+Na]$^+$. In certain cases, depending on the analytical LC/MS results, when an intense ion corresponding to [M+2H]$^{++}$ was detected, the value corresponding to half the calculated molecular mass (MW/2) was also supplied to the FractionLynx software. Under these conditions, collection was also triggered when the mass signal of the ion [M+2H]$^{++}$ and/or [M+Na+H]$^{++}$ were detected.

EXAMPLE 1

3-(1H-indol-2-yl)-1H-thieno[2,3-c]pyrazole-5-(N-phenoxycarboxamide)

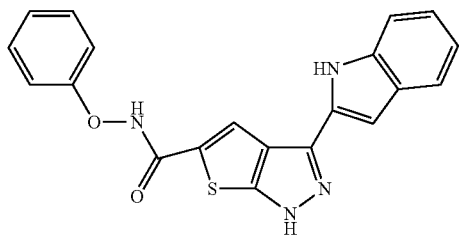

0.165 g (0.37 mmol) of 1-(1-ethoxyethyl)-3-(1H-indol-2-yl)-1H-thieno[2,3-c]pyrazole-5-(N-phenoxycarboxamide) is dissolved with stirring in 20 cm$^3$ of tetrahydrofuran at a temperature in the region of 20° C., to which is added dropwise at 20° C. 18 cm$^3$ (1.8 mmol) of 0.1N hydrochloric acid solution. The reaction mixture is stirred for 15 hours at a temperature in the region of 20° C., followed by dropwise addition, at a temperature in the region of 20° C., of 1.8 cm$^3$ (1.8 mmol) of 1N hydrochloric acid solution. The reaction mixture is stirred for 15 hours at a temperature in the region of 20° C. and is then maintained at 40° C. for 4 hours. 2 cm$^3$ (2 mmol) of 1N hydrochloric acid solution are then run in at a temperature in the region of 20° C. and the reaction mixture is stirred for 15 hours at a temperature in the region of 40° C. The reaction medium is concentrated to dryness under reduced pressure (2.7 kPa) to give a residue, which is taken up in 30 cm$^3$ of water and basified with 2 cm$^3$ (2 mmol) of 0.1N sodium hydroxide solution. Insoluble matter forms, which is taken up in 50 cm$^3$ of dichloromethane. After filtering off the insoluble matter on filter paper, 0.079 g of a yellow solid is obtained, which is purified by flash chromatography on a column of silica gel [(0.04-0.06 mm), eluent: 95/5 dichloromethane/methanol by volume]. After concentrating the fractions containing the expected product to dryness under reduced pressure (2.7 kPa), 0.026 g of 3-(1H-indol-2-yl)-1H-thieno[2,3-c]pyrazole-5-(N-phenoxycarboxamide) is obtained in the form of a yellow solid (DAD-TIC analytical LC/MS purity: 40%), which is purified by preparative LC/MS. After concentrating the fractions containing the expected product to dryness under reduced pressure (2.7 kPa), 0.003 g of 3-(1H-indol-2-yl)-1H-thieno[2,3-c]pyrazole-5-(N-phenoxycarboxamide) is obtained in the form of a yellow solid (DAD-TIC analytical LC/MS purity: 77%) melting at 171° C. LC/MS analysis: mass: M+=374, t (retention)=3.67 min.

1-(1-Ethoxyethyl)-3-(1H-indol-2-yl)-1H-thieno[2,3-c]pyrazole-5-(N-phenoxycarboxamide) may be prepared in the following manner:

0.35 g (0.914 mmol) of 1-(1-ethoxyethyl)-3-(1H-indol-2-yl)-1H-thieno[2,3-c]pyrazole-5-carboxylic acid is dissolved with stirring in 15 cm$^3$ of acetonitrile under argon, at a temperature in the region of 20° C., to which are added 0.266 g (1.83 mmol) of O-phenylhydroxylamine hydrochloride and 0.77 cm$^3$ (5.5 mmol) of triethylamine. The reaction mixture is stirred for 30 minutes at a temperature in the region of 20° C., 0.29 g (0.9 mmol) of O-(1H-benzotriazol-1-yl)-N,N,N',N'-tetramethyluronium-tetrafluoroborate (TBTU) is then added and the mixture is stirred for 15 hours at a temperature in the region of 20° C. 3 cm$^3$ of dimethylformamide and 1 cm$^3$ (7.13 mmol) of triethylamine are then run in and the reaction mixture is stirred for 15 hours at a temperature in the region of 20° C., and is then taken up in 100 cm$^3$ of dichloromethane and 50 cm$^3$ of water. The organic phase is separated out by settling of the phases, washed with saturated potassium hydrogen carbonate solution, dried over magnesium sulfate and then concentrated to dryness under reduced pressure (2.7 kPa). 0.47 g of a pasty brown oil is thus obtained, which is purified by flash chromatography on a column of silica gel [(0.04-0.06 mm), eluent: 98/2 dichloromethane/methanol by volume]. After concentrating to dryness the fractions containing the expected product under reduced pressure (2.7 kPa), 0.165 g of 1-(1-ethoxyethyl)-3-(1H-indol-2-yl)-1H-thieno[2,3-c]pyrazole-5-(N-phenoxycarboxamide) is obtained in the form of a yellow foam melting at 95° C.

1-(1-Ethoxyethyl)-3-(1H-indol-2-yl)-1H-thieno[2,3-c]pyrazole-5-carboxylic acid may be prepared in the following manner:

0.53 g (1.38 mmol) of ethyl 1-(1-ethoxyethyl)-3-(1H-indol-2-yl)-1H-thieno[2,3-c]pyrazole-5-carboxylate is dissolved with stirring in 40 cm$^3$ of ethanol at a temperature in the region of 20° C. 2.8 cm$^3$ (2.8 mmol) of 1N sodium hydroxide solution are then run in, and the resulting solution is then refluxed for 2 hours. The reaction medium is then concentrated to dryness under reduced pressure (2.7 kPa) and the residue is taken up in 30 cm³ of water to which is added 0.17 g of citric acid. The mixture is extracted with twice 50 cm³ of dichloromethane, and acidification of the aqueous phase is continued by addition of citric acid down to pH 2, and the extraction is then continued with twice 50 cm³ of dichloromethane. The various organic phases are combined, dried and then evaporated to dryness under reduced pressure (2.7 kPa). 0.46 g of 1-(1-ethoxyethyl)-3-(1H-indol-2-yl)-1H-thieno[2,3-c]pyrazole-5-carboxylic acid is thus obtained in the form of a yellow solid melting at 204° C.

Ethyl 1-(1-ethoxyethyl)-3-(1H-indol-2-yl)-1H-thieno[2,3-c]pyrazole-5-carboxylate may be prepared in the following manner:

1 g (2.88 mmol) of ethyl 3-bromo-1-(1-ethoxyethyl)-1H-thieno[2,3-c]pyrazole-5-carboxylate is dissolved with stirring in 20 cm³ of dimethylformamide at a temperature in the region of 20° C., which is degassed by sparging with argon. 1 g (3.83 mmol) of N-Boc-indole-2-boronic acid, 0.94 g (2.88 mmol) of cesium carbonate and 0.2 g (0.27 mmol) of 1,1′-bis (diphenylphosphino)-ferrocenedichloropalladium (II) are then added, degassing is continued for 5 minutes and the mixture is then refluxed for 15 hours. The reaction medium is then concentrated to dryness under reduced pressure (2.7 kPa) and the residue is taken up in 100 cm³ of water and 200 cm³ of dichloromethane. The mixture is filtered through Celite® and the phases are separated by settling. The organic phase is dried over magnesium sulfate, filtered and then concentrated to dryness under reduced pressure (2.7 kPa) to give 1.8 g of a black oil, which is purified by flash chromatography on a column of silica gel [(20-45 μm), eluent: 90/10 cyclohexane/ethyl acetate by volume]. After concentrating the fractions containing the expected product to dryness under reduced pressure (2.7 kPa) 0.147 g of ethyl 1-(1-ethoxyethyl)-3-(1H-indol-2-yl)-1H-thieno[2,3-c]pyrazole-5-carboxylate is obtained in the form of a pasty yellow product. ¹H NMR spectrum (300 MHz, (CD₃)₂SO-d₆, δ in ppm): 1.16 (t, J=7 Hz: 3H); 1.37 (t, J=7.5 Hz: 3H); 1.68 (d, J=6.5 Hz: 3H); 3.44 (mt: 1H); 3.64 (mt: 1H); 4.38 (q, J=7.5 Hz: 2H); 5.85 (q, J=6.5 Hz: 1H); 7.04 (resolved t, J=7.5 and 1 Hz: 1H); 7.15 (resolved t, J=7.5 and 1.5 Hz: 1H); 7.20 (d, J=1.5 Hz: 1H); 7.47 (broad d, J=7.5 Hz: 1H); 7.59 (broad d, J=7.5 Hz: 1H); 8.38 (s: 1H); 11.57 (broad s: 1H).

Ethyl 3-bromo-1-(1-ethoxyethyl)-1H-thieno[2,3-c]pyrazole-5-carboxylate may be prepared in the following manner:

1.19 g (3.81 mmol) of 3,5-dibromo-1-(1-ethoxyethyl)-1H-pyrazole-4-carboxaldehyde are introduced with stirring into 50 cm³ of ethanol under an argon atmosphere, at a temperature in the region of 20° C., followed by addition of 0.4 g (3.81 mmol) of sodium carbonate and 0.42 cm³ (3.81 mmol) of ethyl 2-mercaptoacetate. The reaction mixture is then refluxed for 2 hours, and concentrated to dryness under reduced pressure (2.7 kPa). The residue is taken up in 60 cm³ of water and 60 cm³ of dichloromethane, and the phases are separated by settling. The organic phase is dried over magnesium sulfate and then concentrated to dryness under reduced pressure (2.7 kPa). 1.17 g of ethyl 3-bromo-1-(1-ethoxyethyl)-1H-thieno[2,3-c]pyrazole-5-carboxylate are thus obtained in the form of a clear yellow oil that crystallizes to give cream-colored crystals melting at 69° C.

3,5-Dibromo-1-(1-ethoxyethyl)-1H-pyrazole-4-carboxaldehyde may be prepared in the following manner:

1 g (3.94 mmol) of 3,5-dibromo-1H-pyrazole-4-carboxaldehyde, 1.5 cm³ (16 mmol) of ethyl vinyl ether and 3 drops of 12N concentrated hydrochloric acid are introduced with stirring into 30 cm³ of toluene at a temperature in the region of 20° C. The reaction mixture is stirred for 15 hours at a temperature in the region of 20° C., 1.5 cm³ (16 mmol) of ethyl vinyl ether are then run in and stirring is continued for 15 hours at a temperature in the region of 20° C. The reaction mixture is then diluted with 20 cm³ of toluene and washed with twice 30 cm³ of saturated sodium hydrogen carbonate solution. The organic phase is dried over magnesium sulfate and concentrated to dryness under reduced pressure (2.7 kPa) to give 1.19 g of 3,5-dibromo-1-(1-ethoxyethyl)-1H-pyrazole-4-carboxaldehyde in the form of a yellow oil. ¹H NMR spectrum (300 MHz, (CD₃)₂SO-d₆, δ in ppm): 1.10 (t, J=7.5 Hz: 3H); 1.64 (d, J=6.5 Hz: 3H); 3.31 (mt: 1H); 3.51 (mt: 1H); 5.88 (q, J=6.5 Hz: 1H); 9.73 (s: 1H).

3,5-Dibromo-1H-pyrazole-4-carboxaldehyde may be prepared in the following manner:

81.7 g (0.268 mol) of 3,4,5-tribromopyrazole are introduced with stirring into 1500 cm³ of diethyl ether at a temperature in the region of 20° C. and under an argon atmosphere. The mixture is cooled to a temperature in the region of −78° C. and 335 cm³ (0.536 mol) of n-butyllithium at 1.6 mol/l are then added dropwise over 3 hours 15 minutes. The reaction mixture is stirred for 1.5 hours at a temperature in the region of −75° C., followed by dropwise addition of 100 cm³ (1.34 mol) of dimethylformamide, while keeping the temperature below −70° C. Stirring is continued for 2 hours at a temperature in the region of −75° C., and then for 15 hours at a temperature in the region of 20° C. The reaction medium is then cooled in an ice bath and 1000 cm³ of water are added. After separation of the phases by settling, the aqueous phase is extracted with 500 cm³ of diethyl ether and with 3 times 500 cm³ of ethyl acetate. The aqueous phase is then acidified with citric acid solution to pH 3 (the formation of a precipitate is observed) and extracted with twice 1000 cm³ of diethyl ether. The organic phase is dried over magnesium sulfate and concentrated to dryness under reduced pressure (2.7 kPa), and the yellow solid obtained is taken up in 300 cm³ of water and stirred for 2 hours at a temperature in the region of 20° C. The mixture is then filtered and the solid is washed with twice 50 cm³ of water, dried under a ventilated hood and then dried under reduced pressure (2.7 kPa) at a temperature in the region of 40° C. 51.3 g of 3,5-dibromo-1H-pyrazole-4-carboxaldehyde are thus obtained in the form of a yellow powder melting at 173° C.

EXAMPLE 2

3-((E)-styryl-1H-thieno[2,3-c]pyrazole-5-(N-phenoxycarboxamide)

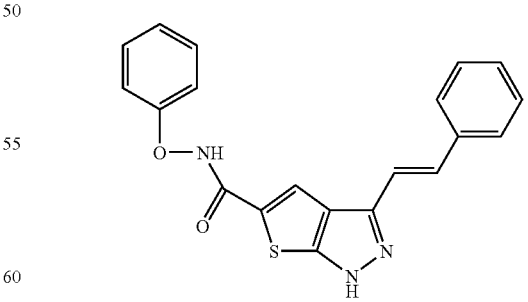

1.5 cm³ (3.0 mmol) of 2N hydrochloric acid solution are added to a solution of 0.083 g (0.191 mmol) of 1-(1-ethoxyethyl)-3-((E)-styryl)-1H-thieno[2,3-c]pyrazole-5-(N-phenoxycarboxamide) in 5 cm³ of tetrahydrofuran, and the solution thus obtained is stirred at a temperature in the region of 25° C. for 48 hours. The reaction medium is then concentrated to dryness under reduced pressure (2.7 kPa) at a temperature in the region of 40° C. and the residue thus obtained is purified by preparative LC-MS. The fractions containing the expected product are combined and concentrated to dryness under reduced pressure (2 kPa) at a temperature in the region of 40° C. The residue is dried at a temperature in the region of 20° C. under reduced pressure (2.7 kPa). 0.030 g of 3-((E)-styryl)-1H-thieno[2,3-c]pyrazole-5-(N-phenoxycarboxamide) is thus obtained in the form of an off-white solid melting at 142° C. Mass spectrum (EI): m/z 361 [M+], m/z 318 and m/z 94 (base peak).

1-(1-Ethoxyethyl)-3-((E)-styryl)-1H-thieno[2,3-c]pyrazole-5-(N-phenoxycarboxamide) may be prepared in the following manner:

0.118 g (1.17 mmol) of triethylamine, 0.089 g (0.61 mmol) of O-phenylhydroxylamine hydrochloride and then 0.197 g (0.61 mmol) of O-(1H-benzotriazol-1-yl)-N,N,N',N'-tetramethyluronium tetrafluoroborate are successively added to a solution containing 0.20 g (0.58 mmol) of 1-(1-ethoxyethyl)-3-((E)-styryl)-1H-thieno[2,3-c]pyrazole-5-carboxylic acid in 10 cm³ of acetonitrile and stirred under argon at a temperature in the region of 25° C. The reaction medium is stirred at a temperature in the region of 20° C. for 24 hours and then heated at a temperature in the region of 80° C. for 3.5 hours. The reaction medium is then cooled to a temperature in the region of 20° C. and thrown into a mixture containing 40 cm³ of brine and 40 cm³ of ethyl acetate, and the phases are separated by settling. The aqueous phase is extracted with twice 40 cm³ of ethyl acetate and the organic extracts are combined, washed successively with 50 cm³ of aqueous SN hydrochloric acid solution, with 50 cm³ of water, with 40 cm³ of saturated aqueous sodium hydrogen carbonate solution and then with 50 cm³ of water, dried over magnesium sulfate, filtered and then concentrated to dryness under reduced pressure (2.7 kPa) at a temperature in the region of 40° C. The residue thus obtained is purified by flash chromatography on a cartridge containing 40 g of silica gel (20 µm spherical), eluting with a cyclohexane/ethyl acetate mixture (75/25 by volume). The fractions containing the expected product are combined and concentrated to dryness under reduced pressure (2 kPa) at a temperature in the region of 40° C. 0.094 g of 1-(1-ethoxyethyl)-3-((E)-styryl)-1H-thieno[2,3-c]pyrazole-5-(N-phenoxycarboxamide) is thus obtained in the form of a red solid. Mass spectrum: EI: m/z 433 [M+], m/z 339: 433-PhO m/z 267 (base peak): 339-C₂H₅—OCH—CH₃ m/z 94: PhO+

1-(1-Ethoxyethyl)-3-((E)-styryl)-1H-thieno[2,3-c]pyrazole-5-carboxylic acid may be prepared in the following manner:

2 cm³ of ethanol, 2 cm³ of water and 0.60 g (10.8 mmol) of potassium hydroxide are successively added with stirring to a solution of 2.0 g (5.4 mmol) of ethyl 1-(1-ethoxyethyl)-3-((E)-styryl)-1H-thieno[2,3-c]pyrazole-5-carboxylate in 15 cm³ of tetrahydrofuran. The reaction medium is heated at a temperature in the region of 85° C. for 5 hours and is then cooled to a temperature in the region of 25° C. and concentrated to dryness under reduced pressure (2.7 kPa) at a temperature in the region of 40° C. The residue is dissolved in 150 cm³ of water and extracted with twice 100 cm³ of diethyl ether. The aqueous phase is acidified to a pH of about 5 by adding solid citric acid, and is then extracted with three times 100 cm³ of ethyl acetate. The organic phases are combined, dried over magnesium sulfate, filtered and then concentrated to dryness under reduced pressure (2.7 kPa) at a temperature in the region of 40° C. 1.8 g of 1-(1-ethoxyethyl)-3-((E)-styryl)-1H-thieno[2,3-c]pyrazole-5-carboxylic acid are thus obtained in the form of a pale yellow solid melting at 160° C. Mass spectrum (EI): m/z 342 [M+], 270 (base peak): [M+] —C₂H₅—O—CH—CH₃.

Ethyl 1-(1-ethoxyethyl)-3-((E)-styryl)-1H-thieno[2,3-c]pyrazole-5-carboxylate may be prepared in the following manner:

1.7 g (1.4 mmol) of tetrakis(triphenylphosphine)-palladium [0], a solution of 6.6 g (43.2 mmol) of trans-β-styreneboronic acid in 40 cm³ of ethanol, and then a solution of 9.2 g (86.4 mmol) of sodium carbonate in 40 cm³ of water are successively added to a solution of 10.0 g (28.8 mmol) of ethyl 3-bromo-1-(1-ethoxyethyl)-1H-thieno[2,3-c]pyrazole-5-carboxylate in 300 cm³ of toluene. The reaction mixture is heated at a temperature in the region of 82° C. for 2.5 hours and is then cooled to a temperature in the region of 25° C. and diluted with 500 cm³ of water and 300 cm³ of ethyl acetate. After separation of the phases by settling, the organic phase is washed successively with twice 300 cm³ of water and then 300 cm³ of saturated brine. The organic phase is then dried over magnesium sulfate, filtered and then concentrated to dryness under reduced pressure (2.7 kPa) at a temperature in the region of 40° C. The residue is purified by chromatography under a pressure of argon (80 kPa), on a cartridge containing 330 g of silica gel (particle size 32-63 µm), eluting with a cyclohexane/ethyl acetate mixture (90/10 by volume). The fractions containing the expected product are combined and concentrated to dryness under reduced pressure (2 kPa) at a temperature in the region of 40° C. 9.3 g of ethyl 1-(1-ethoxyethyl)-3-((E)-styryl)-1H-thieno[2,3-c]pyrazole-5-carboxylate are thus obtained in the form of a yellow solid. (Rf=0.70, thin-layer chromatography on silica gel, eluent: dichloromethane/methanol (98/2 by volume)).

Ethyl 3-bromo-1-(1-ethoxyethyl)-1H-thieno[2,3-c]pyrazole-5-carboxylate is described in Example 1.

EXAMPLE 3

3-[(thiophene-2-carbonyl)amino]-1H-thieno[2,3-c]pyrazole-5-(N-phenoxycarboxamide)hydrochloride

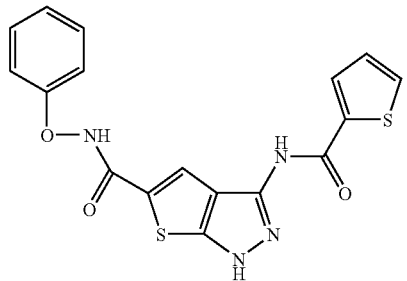

0.66 cm³ (1.32 mmol) of 2N hydrochloric acid is added to a solution of 0.037 g (0.081 mmol) of 1-(1-ethoxyethyl)-3-[(thiophene-2-carbonyl)amino]-1H-thieno[2,3-c]pyrazole-5-(N-phenoxycarboxamide) in 1.7 cm³ of tetrahydrofuran. The reaction mixture is stirred at a temperature in the region of 25° C. for 18 hours and 0.2 cm³ of 2N hydrochloric acid is then added. After 1.5 hours, the reaction mixture is concentrated to dryness under reduced pressure (2.7 kPa) at a temperature in the region of 40° C. and is then taken up in THF and reconcentrated to dryness (operation repeated twice). The residue is dried at a temperature in the region of 20° C. under reduced pressure (2.7 kPa). 34 mg of 3-[(thiophene-2-carbonyl)amino]-1H-thieno[2,3-c]pyrazole-5-(N-phenoxycarboxamide)hydrochloride are thus obtained in the form of an amorphous greenish solid. (Rf=0.37, thin-layer chromatography on silica gel, eluent: dichloromethane/methanol (90/10 by volume)). Mass spectrum (EI): m/z 384 [M$^+$], m/z 341, m/z 111 (base peak), and m/z 94.

1-(1-Ethoxyethyl)-3-[(thiophene-2-carbonyl)amino]-1H-thieno[2,3-c]pyrazole-5-(N-phenoxycarboxamide) may be prepared in the following manner:

0.119 g (1.18 mmol) of triethylamine, 0.090 g (0.62 mmol) of O-phenylhydroxylamine hydrochloride and then 0.198 g (0.62 mmol) of O-(1H-benzotriazol-1-yl)-N,N,N',N'-tetramethyluronium tetrafluoroborate are successively added to a solution containing 0.22 g (0.59 mmol) of 1-(1-ethoxyethyl)-3-[(thiophene-2-carbonyl)amino]-1H-thieno[2,3-c]pyrazole-5-carboxylic acid in 11 cm$^3$ of acetonitrile and stirred under argon at a temperature in the region of 25° C. The reaction medium is stirred at a temperature in the region of 80° C. for 30 minutes, then at a temperature in the region of 20° C. for 30 minutes and finally at a temperature in the region of 80° C. for 30 minutes. The reaction medium is then cooled to a temperature in the region of 20° C. and thrown into a mixture containing 40 cm$^3$ of brine and 40 cm$^3$ of ethyl acetate, and the phases are separated by settling. The aqueous phase is extracted with twice 40 cm$^3$ of ethyl acetate and the organic extracts are combined, washed successively with 50 cm$^3$ of aqueous 2N hydrochloric acid solution, with 50 cm$^3$ of water, with 40 cm$^3$ of saturated aqueous sodium hydrogen carbonate solution and then with 40 cm$^3$ of water, dried over magnesium sulfate, filtered and then concentrated to dryness under reduced pressure (2.7 kPa) at a temperature in the region of 40° C. The residue thus obtained is purified by flash chromatography on a column containing 30 g of silica gel (40-63 μm), eluting with a dichloromethane/methanol mixture (98/2 by volume) and then on a column containing 30 g of silica gel (40-63 μm), eluting with a cyclohexane/ethyl acetate mixture (70/30 by volume). The fractions containing the expected product are combined and concentrated to dryness under reduced pressure (2 kPa) at a temperature in the region of 40° C. The residue is purified by chromatography on preparative plates. 0.040 g of 1-(1-ethoxyethyl)-3-[(thiophene-2-carbonyl)amino]-1H-thieno[2,3-c]pyrazole-5-(N-phenoxycarboxamide) is thus obtained in the form of a yellow solid. (Rf=0.56, thin-layer chromatography on silica gel, eluent: cyclohexane/ethyl acetate (50/50 by volume)).

1-(1-Ethoxyethyl)-3-[(thiophene-2-carbonyl)amino]-1H-thieno[2,3-c]pyrazole-5-carboxylic acid may be prepared in the following manner: batch P-32079-158-1

1 cm$^3$ of ethanol, 1 cm$^3$ of water and 0.29 g (5.1 mmol) of potassium hydroxide are successively added with stirring to a solution of 1.0 g (2.3 mmol) of ethyl 1-(1-ethoxyethyl)-3-[(thiophene-2-carbonyl)amino]-1H-thieno[2,3-c]pyrazole-5-carboxylate in 8 cm$^3$ of tetrahydrofuran. The reaction medium is heated at a temperature in the region of 85° C. for 2 hours and is then cooled to a temperature in the region of 25° C. and concentrated to dryness under reduced pressure (2.7 kPa) at a temperature in the region of 40° C. The residue is dissolved in water and extracted with diethyl ether. The aqueous phase is acidified to a pH of about 5-6 by adding solid citric acid, and is then extracted three times with ethyl acetate. The organic phases are combined, dried over magnesium sulfate, filtered and then concentrated to dryness under reduced pressure (2.7 kPa) at a temperature in the region of 40° C. 0.25 g of 1-(1-ethoxyethyl)-3-[(thiophene-2-carbonyl)amino]-1H-thieno[2,3-c]pyrazole-5-carboxylic acid is thus obtained in the form of a yellowish solid. Acidification of the aqueous phase to a pH of about 3-4, followed by the same treatment allows a second fraction of 0.25 g of 1-(1-ethoxyethyl)-3-[(thiophene-2-carbonyl)amino]-1H-thieno[2,3-c]pyrazole-5-carboxylic acid to be obtained in the form of a yellowish solid. (Rf=0.15, thin-layer chromatography on silica gel, eluent: dichloromethane/methanol (90/10 by volume)).

Ethyl 1-(1-ethoxyethyl)-3-[(thiophene-2-carbonyl)-amino]-1H-thieno[2,3-c]pyrazole-5-carboxylate may be prepared in the following manner:

1.1 g (5.8 mmol) of copper(I) iodide, 0.69 cm$^3$ (5.8 mmol) of trans-1,2-diaminocyclohexane, 4.4 g (34.6 mmol) of 2-thiophenecarboxamide and then 12.2 g (57.6 mmol) of tripotassium phosphate are successively added to a solution of 10.0 g (28.8 mmol) of ethyl 3-bromo-1-(1-ethoxyethyl)-1H-thieno[2,3-c]pyrazole-5-carboxylate in 167 cm$^3$ of dioxane, stirred at a temperature in the region of 25° C., under argon. The reaction mixture is refluxed for 20 hours and is then cooled to a temperature in the region of 25° C. and filtered through Clarcel®. The solid is washed with twice 170 cm$^3$ of ethyl acetate. The filtrate is extracted with three times 170 cm$^3$ of saturated brine and the organic phase is then dried over sodium sulfate, filtered and then concentrated to dryness under reduced pressure (2.7 kPa) at a temperature in the region of 35° C. The residue is purified by chromatography on a column of about 300 g of silica gel (particle size 40-63 μm), eluting with a cyclohexane/ethyl acetate mixture (90/10 and then 85/15 by volume). The fractions containing the expected product are combined and concentrated to dryness under reduced pressure (2 kPa) at a temperature in the region of 40° C. 2.9 g of ethyl 1-(1-ethoxyethyl)-3-[(thiophene-2-carbonyl)amino]-1H-thieno[2,3-c]pyrazole-5-carboxylate are thus obtained in the form of a yellow solid. (Rf=0.18, thin-layer chromatography on silica gel, eluent: cyclohexane/ethyl acetate (80/20 by volume)).

Ethyl 3-bromo-1-(1-ethoxyethyl)-1H-thieno[2,3-c]pyrazole-5-carboxylate is described in Example 1.

The products according to the invention may be in achiral form, or racemic form, or in the form enriched in one stereoisomer, or enriched in one enantiomer; and may optionally be salified.

A product in accordance with the invention may be used for the manufacture of a medicament that is useful for treating a pathological condition, in particular a cancer.

The present invention also relates to therapeutic compositions comprising a compound according to the invention, in combination with a pharmaceutically acceptable excipient according to the chosen mode of administration. The pharmaceutical composition may be in solid or liquid form or in the form of liposomes.

Among the solid compositions that may be mentioned are powders, gel capsules and tablets. Among the oral forms that may also be included are solid forms protected with respect to the acidic medium of the stomach. The supports used for the solid forms consist especially of mineral supports, for instance phosphates or carbonates, or organic supports, for instance lactose, celluloses, starch or polymers. The liquid forms consist of solutions, suspensions or dispersions. They contain as dispersive support either water or an organic solvent (ethanol, NMP or the like) or mixtures of surfactants and of solvents, or of complexing agents and of solvents.

The liquid forms will preferably be injectable and, as a result, will have a formulation that is acceptable for such a use.

Routes of administration that are acceptable by injection include intravenous, intraperitoneal, intramuscular and subcutaneous routes, the intravenous route being preferred.

The administered dose of the compounds of the invention will be adapted by the practitioner as a function of the route of administration to the patient and of the patient's condition.

The compounds of the present invention may be administered alone or as a mixture with other anticancer agents. Among the possible combinations that may be mentioned are:

alkylating agents and especially cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine platinum derivatives such as, especially, cisplatin, carboplatin or oxaliplatin antibiotics such as, especially, bleomycin, mitomycin or dactinomycin antimicrotubule agents such as, especially, vinblastine, vincristine, vindesine, vinorelbine and taxoids (paclitaxel and docetaxel)

anthracyclines such as, especially, doxorubicin, daunorubicin, idarubicin, epirubicin, mitoxantrone and losoxantrone group I and II topoisomerase inhibitors such as etoposide, teniposide, amsacrine, irinotecan, topotecan and tomudex fluoropyrimidines such as 5-fluorouracil, UFT and floxuridine cytidine analogs such as 5-azacytidine, cytarabine, gemcitabine, 6-mercaptomurine and 6-thioguanine adenosine analogs such as pentostatin, cytarabine or fludarabine phosphate methotrexate and folinic acid various enzymes and compounds such as L-asparaginase, hydroxyurea, trans-retinoic acid, suramine, dexrazoxane, amifostine and herceptin, and also estrogen-based and androgenic hormones antivascular agents such as combretastatin derivatives or colchicine derivatives, and prodrugs thereof.

It is also possible to combine the compounds of the present invention with a radiation treatment. These treatments may be administered simultaneously, separately or sequentially. The treatment will be adapted by the practitioner as a function of the patient to be treated.

The progress of the cell cycle is often governed by cycline-dependent kinases (CDK), which are activated by an interaction with proteins belonging to the cycline family, this activation ending in the phosphorylation of substrates and finally in cell division. In addition, the endogenous inhibitors of the CDKs that are activated (family of INK4 and of KIP/CIP) negatively regulate the activity of CDKs. The growth of normal cells is due to a balance between the CDK activators (cyclines) and the endogenous inhibitors of CDKs. In several types of cancer, the aberrant expression or activity of several of these cell cycle regulators has been described.

Cycline E activates the kinase Cdk2, which then acts to phosphorylate the protein pRb (retinoblastoma protein) resulting in an irreversible engagement in cell division and transition to the S phase (PL Toogood, Medicinal Research Reviews (2001), 21(6); 487-498. The kinase CDK2 and possibly CDK3 are necessary for progress into the G1 phase and entry into the S phase. During the formation of a complex with cycline E, they maintain the hyperphosphorylation of pRb to aid the progress from the G1 phase to the S phase. In complexes with cycline A, CDK2 plays a role in inactivating E2F and is necessary for achieving the S phase (T D. Davies et al. (2001) Structure 9, 389-3).

The CDK1/cycline B complex regulates the progress of the cell cycle between the G2 phase and the M phase. Negative regulation of the CDK/cycline B complex prevents normal cells from entering the S phase before the G2 phase has been correctly and completely terminated (K. K. Roy and E. A. Sausville, Current Pharmaceutical Design, 2001, 7, 1669-1687).

A level of regulation of the activity of CDKs exists. The cycline-dependent activators of kinases (CAK) have a positive action on regulating CDKs. CAK phosphorylates CDKs on the threonine residue to make the target enzyme totally active.

The presence of defects in the molecules involved in the cell cycle results in activation of the CDKs and progression of the cycle; it is normal to wish to inhibit the activity of the CDK enzymes in order to block the cell growth of cancer cells.

Many proteins involved in chromosome segregation and spindle assembly have been identified in yeast and *drosophila*. Disorganization of these proteins leads to the non-segregation of the chromosomes and to monopolar or disorganized spindles. Among these proteins, certain kinases, including Aurora and Ip11, originating, respectively, from *drosophila* and from *S. cerevisiae*, are necessary for chromosome segregation and separation of the centrosome. A human analog of yeast Ip11 has recently been cloned and characterized by various laboratories. This kinase, known as aurora2, STK15 or BTAK, belongs to the serine/threonine kinase family. Bischoff et al. have shown that Aurora2 is oncogenic, and is amplified in human colorectal cancers (EMBO J, 1998, 17, 3052-3065). This has also been illustrated in cancers involving epithelial tumors such as breast cancer.

The present invention concerns novel benzothiazole derivatives. The invention thus relates to the use of benzothiazole derivatives as agents for inhibiting kinases and more particularly as anticancer agents. Among these, the invention preferentially relates to the sulfonic esters of benzothiazoles. The invention also relates to the use of said derivatives for the preparation of a medicament for treating man.

PLK

The "Polo-Like Kinases" or "PLKs" belong to the family of serine/threonine kinases, and play an essential role in regulating the cell cycle, especially in the phases of entering and exiting mitosis. The PLKs include PLK1, PLK2, PLK3 and PLK4.

The PLKs are known for their essential role in mitosis in many species (for example bacteria, *drosophila* and *xenopes*). RNAi experiments on *drosophila* have demonstrated that suppression of polo leads to cellular arrest in G2/M phase and to apoptosis. PLK1 is the human polo homolog. During mitosis, it has been demonstrated that PLK1 plays a role in the maturation of centrosomes and in the dynamics of the microtubules involved in the formation of the mitotic spindle. PLK1 is also involved in the exiting of mitosis of cells. PLK1 probably also has a role in cytokinesis.

It has also been demonstrated that the overexpression of PLK1 is a factor of poor prognosis in the case of cancer.

All these studies suggest that an inhibitor of the kinase activity of PLK1 may make it possible to inhibit anarchic cell proliferation in the field of oncology.

The present patent application thus relates particularly to novel inhibitors of the PLK1 receptor that may be used especially for treating abnormal proliferation of cells, especially in oncology.

Tie-2 (TEK) is a member of a family of tyrosine kinase receptors, which is specific to endothelial cells. Tie2 is the first receptor with tyrosine kinase activity for which both the agonist (angiopoietin 1 or Ang1), which stimulates the autophosphorylation of the receptor and cell signaling [S. Davis et al. (1996) Cell 87, 1161-1169], and the antagonist (angiopoietin 2 or Ang2) [P. C. Maisonpierre et al. (1997) Science 277, 55-60] are known. Angiopoietin 1 can synergize with VEGF in the final stages of neoangiogenesis [Asahara T. Circ. Res. (1998) 233-240]. Knockout experiments and transgenic manipulations of the expression of Tie2 or of Ang1 lead to animals that present vascularization defects [D. J. Dumont et al. (1994) Genes Dev. 8, 1897-1909 and C. Suri (1996) Cell 87, 1171-1180]. The binding of Ang1 to its receptor leads to autophosphorylation of the kinase domain of Tie2, which is essential for neovascularization and also for the recruitment and interaction of blood vessels with the pericytes and smooth muscle cells; these phenomena contribute towards the maturation and stability of the newly formed blood vessels [P. C. Maisonpierre et al. (1997) Science 277, 55-60]. Lin et al. (1997) J. Clin. Invest. 100, 8: 2072-2078 and Lin P. (1998) PNAS 95, 8829-8834 have shown an inhibition of tumor growth and vascularization, and also a reduction in lung metastases, during adenoviral infections or injections of the extracellular domain of Tie-2 (Tek) into models of melanoma and breast tumor xenografts.

Tie2 inhibitors may be used in situations in which neovascularization takes place inappropriately (i.e. in diabetic retinopathy, chronic inflammation, psoriasis, Kaposi's sarcoma, chronic neovascularization due to macular degeneration, rheumatoid arthritis, infantile hemoangioma and cancers).

FAK is a cytoplasmic tyrosine kinase that plays an important role in transducing the signal transmitted by the integrins, a family of heterodimeric cellular adhesion receptors. FAK and the integrins are colocated in perimembrane structures known as adhesion plaques. It has been shown in many cell types that the activation of FAK and its phosphorylation on tyrosine residues and in particular its autophosphorylation on tyrosine 397 are dependent on the binding of integrins to their extracellular ligands and thus induced during cellular adhesion [Kornberg L, et al. J. Biol. Chem. 267(33): 23439-442 (1992)]. Autophosphorylation on tyrosine 397 of FAK represents a binding site for another tyrosine kinase, Src, via its SH2 domain [Schaller et al. Mol. Cell. Biol. 14: 1680-1688. 1994; Xing et al. Mol. Cell. Biol. 5: 413-421. 1994]. Src may then phosphorylate FAK on tyrosine 925, thus recruiting the adapter protein Grb2 and inducing in certain cells activation of the ras and MAP kinase pathway involved in controlling cell proliferation [Schlaepfer et al. Nature; 372: 786-791. 1994; Schlaepfer et al. Prog. Biophy. Mol. Biol. 71: 435-478. 1999; Schlaepfer and Hunter, J. Biol. Chem. 272: 13189-13195. 1997]. The activation of FAK may also induce the jun NH2-terminal kinase (JNK) signaling pathway and result in the progression of cells towards the G1 phase of the cell cycle [Oktay et al., J. Cell. Biol. 145: 1461-1469. 1999]. Phosphatidylinositol-3-OH kinase (PI3-kinase) also binds to FAK on tyrosine 397 and this interaction might be necessary for activating PI3-kinase [Chen and Guan, Proc. Nat. Acad. Sci. USA. 91: 10148-10152. 1994; Ling et al. J. Cell. Biochem. 73: 533-544. 1999]. The FAK/Src complex phosphorylates various substrates, for instance paxillin and p130CAS in fibroblasts [Vuori et al. Mol. Cell. Biol. 16: 2606-2613. 1996].

The results of numerous studies support the hypothesis that FAK inhibitors might be useful in treating cancer. Studies have suggested that FAK might play an important role in cell proliferation and/or survival in vitro. For example, in CHO cells, some authors have demonstrated that the overexpression of p125FAK leads to an acceleration of the transition G1 to S, suggesting that p125FAK promotes cell proliferation [Zhao J.-H et al. J. Cell Biol. 143: 1997-2008. 1998].

Other authors have shown that tumor cells treated with FAK antisense oligonucleotides lose their adhesion and enter into apoptosis (Xu et al., Cell Growth Differ. 4: 413-418. 1996). It has also been demonstrated that FAK promotes the migration of cells in vitro. Thus, fibroblasts that are deficient for FAK expression (FAK "knockout" mice) show a rounded morphology and deficiencies in cellular migration in response to chemotactic signals, and these defects are eliminated by re-expression of FAK [D J. Sieg et al., J. Cell Science. 112: 2677-91. 1999]. Overexpression of the C-terminal domain of FAK (FRNK) blocks the stretching of adherent cells and reduces cell migration in vitro [Richardson A. and Parsons J. T. Nature. 380: 538-540. 1996]. Overexpression of FAK in CHO or COS cells or in human astrocytoma cells promotes migration of the cells. The involvement of FAK in promotion of the proliferation and migration of cells in many cell types in vitro suggests the potential role of FAK in neoplastic processes. A recent study has effectively demonstrated the increase in the proliferation of tumor cells in vivo after inducing the expression of FAK in human astrocytoma cells [Cary L. A. et al. J. Cell Sci. 109: 1787-94. 1996; Wang D et al. J. Cell Sci. 113: 4221-4230. 2000]. Furthermore, immunohistochemical studies of human biopsies have demonstrated that FAK was overexpressed in prostate cancer, breast cancer, thyroid cancer, colon cancer, melanoma, brain cancer and lung cancer, the level of expression of FAK being directly correlated to the tumors showing the most aggressive phenotype [Weiner T M, et al. Lancet. 342 (8878): 1024-1025. 1993; Owens et al. Cancer Research. 55: 2752-2755. 1995; Maung K. et al. Oncogene. 18: 6824-6828. 1999; Wang D et al. J. Cell Sci. 113: 4221-4230. 2000].

KDR (Kinase insert Domain Receptor), also known as VEGF-R2 (Vascular Endothelial Growth Factor Receptor 2), is expressed solely in endothelial cells. This receptor binds to the angiogenic growth factor VEGF, and thus serves as a transduction signal mediator via the activation of its intracellular kinase domain. The direct inhibition of the kinase activity of VEGF-R2 makes it possible to reduce the phenomenon of angiogenesis in the presence of exogenous VEGF (Vascular Endothelial Growth Factor) (Strawn et al., Cancer Research, 1996, vol. 56, p. 3540-3545). This process has especially been demonstrated using VEGF-R2 mutants (Millauer et al., Cancer Research, 1996, vol. 56, p. 1615-1620). The VEGF-R2 receptor appears to have no other function in adults than that associated with the angiogenic activity of VEGF. Thus, a selective inhibitor of the kinase activity of VEGF-R2 should show only little toxicity.

In addition to this central role in the dynamic angiogenic process, recent results suggest that the expression of VEGF contributes towards the survival of tumoral cells after chemotherapy and radiotherapy, underlining the potential synergy of KDR inhibitors with other agents (Lee et al. Cancer Research, 2000, vol. 60, p. 5565-5570).

Experimental Protocols on the Biochemical Tests

1. Aurora2

The inhibitory effect of the compounds toward the kinase Aurora2 is determined via a radioactivity scintillation test using nickel chelate.

A complete recombinant Aurora2 enzyme, the N-terminal of which was labeled with histidine, was expressed in *E. coli* and purified to a quality close to homogeneity.

The C-terminal fragment (Q1687-H2101) of an NuMA (Nuclear protein which is associated with the Mitotic Apparatus) expressed in *E. coli*, and the N-terminal end of which was labeled with histidine, was purified by nickel chelate chromatography and used as substrate in the Aurora2 kinase test.

To determine the kinase activity, the substrate NuMA is equilibrated by chromatography on a PD10 Pharmacia column, in a buffer (50 mM Tris-HCl, pH 7.5, 50 mM NaCl, 10 mM $MgCl_2$) supplemented with 10% (v/v) of glycerol and 0.05% (w/v) of NP40.

The kinase activity of Aurora2 is measured by scintillation with nickel chelate (New England Nuclear, SMP107 model). Each well contains 100 µl of the following solution: 0.02 µM of Aurora2; 0.5 µM of NuMA substrate; 1 µM of ATP supplemented with 0.5 µCi of ATP-[$^{33}$P]. The solutions are incubated for 30 minutes at 37° C. The test buffer is then removed and the wells are rinsed twice with 300 µl of kinase buffer. The radioactivity is measured in each well using a Packard Model Top Count NXT machine.

The background noise is deduced by measuring radioactivity measured in duplicate in wells containing the radioactive ATP alone containing buffered kinase treated in the same manner as for the other samples.

The activity of the control is determined by measuring in duplicate the radioactivity in the complete test mixture (ATP, Aurora2 and substrate NuMA), in the absence of test compound.

The inhibition of the activity of Aurora2 with a compound of the invention is expressed as a percentage of inhibition of the control activity in the absence of test compound. Staurosporin is added to each plate as inhibition control.

2. CDK2/cycline E:

Purification of the CDK2/cyclineE-(His)$_6$ Complex by IMAC (Immobilized Metal Affinity Chromatography):

Two recombinant baculoviruses bearing the human sequences coding, respectively, for CDK2 and cyclineE (the latter bearing a C-terminal hexahistidine tag) are used to coinfect Sf21 insect cells. Two to three days after the start of coinfection, the cells are harvested by centrifugation and then stored at −40° C. until the time of use. After thawing and mechanical lysis of the cells, the complex present in the lysis supernatant is purified by affinity chromatography on nickel (IMAC), and stored at −80° C.

CDK2/cyclineE Flashplate Test in 96-Well Format.

A format in streptavidin-coated 96-well plates is used to test the activity of the compounds on the kinase activity of CDK2/cycline E.

To perform this test, the biotinylated peptide substrate, a fragment of the protein pRb (biotinyl-SACPLNLPLQN-NHTAADMYLSPVRSPKKKGSTTR—OH) (SEQ ID NO: 1), is dissolved at a concentration of 1 mM in kinase buffer (HEPES/NaOH 50 mM, NaCl 1 mM, $MgCl_2$ 5 mM, pH 7.5) in order to constitute a stock solution stored at −20° C. in the form of 110 µL aliquots. On the day of the experiment, an aliquot of this solution is thawed and diluted in kinase buffer containing 1 mM of dithiothreitol, added to the buffer extemporaneously, in order to obtain a concentration of 14.3 µM. 70 µL of this solution are added to each well of the Flashplate in order to obtain a final substrate concentration of 10 µM during the enzymatic reaction performed in a final volume of the reaction medium of 100 µL (cf. below).

Intermediate dilutions of inhibitors (products of the invention) at various concentrations are prepared in DMSO from stock solutions at 10 mM in separate tubes. Dilutions at 1000 µM, 333.3 µM, 111.1 µM, 37.03 µM, 12.35 µM, 4.11 µM and 1.37 µM are thus prepared. One µL of each of these solutions (or 1 µL of DMSO for the controls) is transferred into the wells of the test plate.

19 µl of a solution of a mixture of adenosine triphosphate (ATP) and of ATPγ$^{33}$P in kinase buffer at a total concentration of 5.26 µM of ATP and 52.6 µCi/ml of $^{33}$P are then added to each well. The enzymatic reaction is initiated by adding 10 µL per well of a 200 nM solution of CDK2/cycline E in kinase buffer containing 1 mM of dithiothreitol (or 10 µL of kinase buffer containing 1 mM of dithiothreitol for the reaction blanks).

After addition of each of the reagents, the final volume of each well is 100 µL, the final concentration of substrate is 10 µM, the final inhibitor concentrations are 10 µM, 3.33 µM, 1.11 µM, 0.37 µM, 0.123 µM, 0.041 µM and 0.014 µM (according to the concentration of the intermediate dilution), the final ATP concentration is 1 µM, the final amount of $^{33}$P is 1 µCi/well, and the final concentration of CDK2/cycline E complex is 20 nM.

After addition of all of the reagents, the test plate is incubated at 30° C. with orbital shaking at 650 rpm.

When the incubation is complete, the plate is washed three times with 300 µL per well of PBS (phosphate-buffered saline, pH=7.4, without calcium or magnesium, reference 10010-015, Gibco BRL). The incorporation of $^{33}$P to the peptide is quantified by scintillation counting with a Packard Topcount.NXT machine. The inhibitory activity of the products of the invention is evaluated by measuring the inhibitory concentration that allows a 50% reduction in the enzymatic activity ($IC_{50}$).

3. Tie2

The coding sequence of human Tie2 corresponding to the amino acids of the intracellular domain 776-1124 was generated by PCR using the cDNA isolated from a human placenta as a model. This sequence was introduced into a pFastBacGT baculovirus expression vector in the form of a GST fusion protein.

The inhibitory effect of the molecules is determined in a test of phosphorylation of PLC with Tie2 in the presence of GST-Tie2 purified to about 80% homogeneity. The substrate is composed of the SH2-SH3 fragments of PLC expressed in the form of a GST fusion protein.

The kinase activity of Tie2 is measured in a MOPS 20 mM pH 7.2 buffer, containing 10 mM $MgCl_2$, 10 mM $MnCl_2$, 1 mM DTT, 10 mM of glycerophosphate. In a 96-well FlashPlate plate maintained on ice, a reaction mixture is deposited, composed of 70 µL of kinase buffer containing 100 ng of enzyme GST-Tie2 per well. Next, 10 µL of the test molecule diluted in DMSO to a maximum concentration of 10% are added. For a given concentration, each measurement is performed four times. The reaction is initiated by adding 20 µL of solution containing 2 µg of GST-PLC, 2 µm of cold ATP and 1 µCi of $^{33}$P [ATP]. After incubation for one hour at 37° C., the reaction is stopped by adding 1 volume (100 µl) of 200 mM EDTA. After removal of the incubation buffer, the wells are washed three times with 300 µL of PBS. The radioactivity is measured on a MicroBeta1450 Wallac.

The inhibition of the Tie2 activity is calculated and expressed as a percentage of inhibition relative to the control activity determined in the absence of compound.

Activity of the Prepared Products:

The activity of the products was determined by measuring the inhibition of Aurora2 activity. The results are given in Table 1 below (IC50, nM):

TABLE 1

| Example | Structure | Aurora2 | CDK2 | Tie2 |
|---|---|---|---|---|
| 1 | (phenoxy-NH-C(=O)-thienopyrazole-3-(1H-indol-3-yl)) | <50 | <100 | — |
| 2 | (phenoxy-NH-C(=O)-thienopyrazole-3-styryl) | <50 | 521.7 | — |
| 3 | (phenoxy-NH-C(=O)-thienopyrazole-3-NHC(=O)-thiophene) | <50 | <500 | <500 |

What is claimed is:

1. A compound of general formula (I):

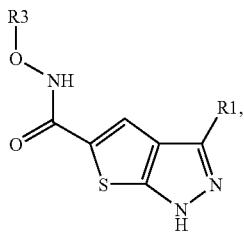

wherein:
(i) R1 is independently selected from the group consisting of R2, NHCO(R2), —CH=CH—(R2), and NH—R4, in which R2 is independently selected from the group consisting of —(C1-C24)alkyl, —(C3-C9)cycloalkyl, heterocycloalkyl, heterocycloalkylene, aryl, heteroaryl, arylalkyl, and heteroarylalkyl;
(ii) R3 is independently selected from the group consisting of —(C1-C6)alkyl, —(C1-C6)alkylaryl, —(C1-C6) alkylheteroaryl, -aryl, and -heteroaryl;
(iii) R4 represents aryl, heteroaryl, —(C3-C9)cycloalkyl, or heterocycloalkyl;
the radicals R2, R3 and R4 being optionally substituted with one or more radicals, which may be identical or different, chosen from halogen, hydroxyl, alkoxy, cycloalkyl, NH2, NHAlk, N(Alk)2, alkyl, hydroxyalkyl, heterocycloalkyl and phenyl, which is itself optionally substituted with one or more radicals, which may be identical or different, chosen from halogen, hydroxyl, NH2, alkoxy, alkyl and hydroxyalkyl radicals;
with the proviso that when R3 is —(C1-C6)alkyl, then R1 is not: aryl, heteroaryl or —CH=CH—(R2), in which R2 is selected from the group consisting of aryl and heteroaryl;
or an addition salt of said compound with a mineral or organic acid or with a mineral or organic base;
or a racemic mixture, enantiomer, diastereoisomer or mixture thereof of said compound or said salt;
with the exception of the compound 3-((E)-styryl-1H-thieno[2,3-c]pyrazole-5-(N-phenoxycarboxamide.

2. The compound of general formula (I) according to claim 1, wherein:
(i) R1 is independently selected from the group consisting of R2, NHCO(R2), and —CH=CH—(R2), in which R2 is independently selected from the group consisting of —(C1-C24)alkyl, —(C3-C9)cycloalkyl, heterocycloalkyl, heterocycloalkylene, aryl, heteroaryl, arylalkyl, and heteroarylalkyl;
(ii) R3 is independently selected from the group consisting of —(C1-C6)alkyl, —(C1-C6)alkylaryl, —(C1-C6) alkylheteroaryl, -aryl, and -heteroaryl;
with the proviso that when R3 is —(C1-C6)alkyl, then R1 is not: aryl, heteroaryl or —CH=CH—(R2), in which R2 is selected from the group consisting of aryl and heteroaryl.

3. The compound according to claim 1, wherein R1 is chosen from aryl, heteroaryl, NHCO(R2) and NH—R4, with R2 being independently selected from the group consisting of —(C1-C24)alkyl, —(C3-C9)cycloalkyl, heterocycloalkyl, heterocycloalkylene, aryl, heteroaryl, arylalkyl, and heteroarylalkyl; and R4 represents aryl, heteroaryl, —(C3-C9) cycloalkyl or heterocycloalkyl.

4. The compound according to claim 1, wherein R1 represents NH—R4, with R4 representing aryl, heteroaryl, —(C3-C9)cycloalkyl or heterocycloalkyl.

5. The compound according to claim 1, wherein R1 is chosen from aryl and heteroaryl.

6. The compound according to claim 1, wherein R1 is —CH=CH—(R2), in which R2 is chosen from aryl and heteroaryl.

7. The compound according to claim 1, wherein R1 is NHCO(R2).

8. The compound according to claim 1, wherein R3 is aryl or heteroaryl.

9. The compound according to claim 1, wherein the aryl are each phenyl and the heteroaryl are each independently chosen from pyridyl, indolyl, benzimidazolyl, pyrazolyl and pyrrolyl.

10. The compound according to claim 8, wherein the aryl are each phenyl and the heteroaryl are each independently chosen from pyridyl, indolyl, benzimidazolyl, pyrazolyl and pyrrolyl.

11. The compound according to claim 1, selected from the group consisting of:
3-(1H-indol-2-yl)-1H-thieno[2,3-c]pyrazole-5-(N-phenoxycarboxamide), and
3-[(thiophene-2-carbonyl)amino]-1H-thieno[2,3-c]pyrazole-5-(N-phenoxycarboxamide);
or a pharmaceutically acceptable salt thereof.

12. The compound according to claim 1, which is in:
1) achiral form, or
2) racemic form, or
3) a form enriched in one stereoisomer, or
4) a form enriched in one enantiomer;
and in that it is optionally salified.

13. A process for preparing a compound of general formula (I) according to claim 1:

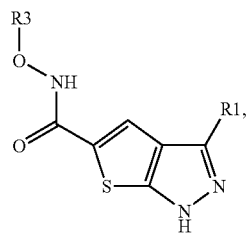

in which R1 is NHCO(R2), and R2 and R3 are as defined in claim 1, comprising the steps of
(i) coupling between:
(i-a) an amine of general formula (X):

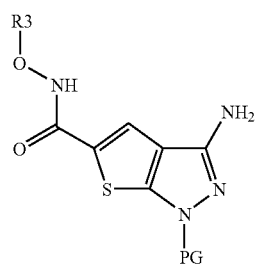

in which R3 is as defined above, and in which PG is a protecting group for the free endocyclic NH function of the thieno[2,3-c]pyrazole nucleus, and (i-b) a carboxylic acid R2—COOH in the presence of a coupling agent or a carboxylic acid derivative, in the presence of a base; and then (ii) cleaving the PG.

14. The process according to claim 13, wherein the carboxylic acid derivative is selected from an acid chloride and an anhydride.

15. The process according to claim 13, wherein the base is selected from a tertiary amine and an alkali metal carbonate.

16. The process according to claim 13, wherein the amine of general formula (X) is obtained by protection of the NH function of the pyrazole nucleus of a product of general formula (IX):

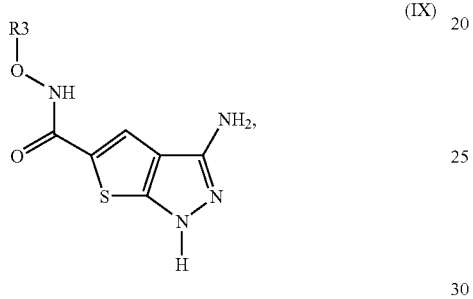
(IX)

in which R3 is as defined in claim 13.

17. The process according to claim 16, wherein the product of general formula (IX) is obtained by reaction between:

(i) R3ONH₂, in which R3 is as defined in claim 16, in the presence of a trialkylaluminum, and (ii) a product of general formula (XIV):

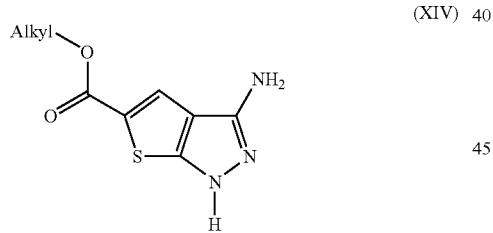
(XIV)

in which alkyl is (C1-C6)alkyl.

18. The process according to claim 17, wherein the triakylaluminum is trimethylaluminum.

19. A process for preparing a compound of general formula (Ia) or (IIIa) below:

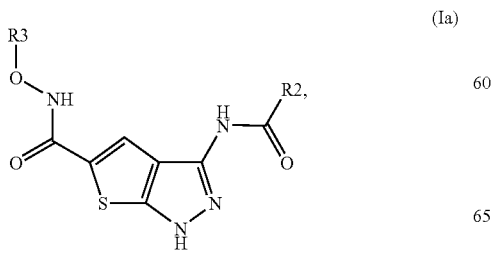
(Ia)

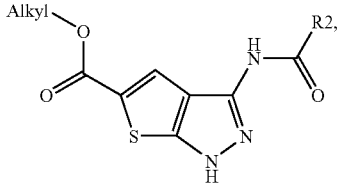
(IIIa)

in which R2 is independently selected from the group consisting of —(C1-C24)alkyl, —(C3-C9)cycloalkyl, heterocycloalkyl, heterocycloalkylene, aryl, heteroaryl, arylalkyl, and heteroarylalkyl; and R3 is independently selected from the group consisting of —(C1-C6)alkyl, —(C1-C6)alkylaryl, —(C1-C6)alkylheteroaryl, -aryl, and -heteroaryl; the radicals R2 and R3 being optionally substituted with one or more radicals, which may be identical or different, chosen from halogen, hydroxyl, alkoxy, cycloalkyl, NH2, NHAlk, N(Alk)2, alkyl, hydroxyalkyl, heterocycloalkyl and phenyl, which is itself optionally substituted with one or more radicals, which may be identical or different, chosen from halogen, hydroxyl, NH2, alkoxy, alkyl and hydroxyalkyl radicals;

and alkyl is (C1-C6)alkyl;

comprising the steps of:

(i) coupling between:

(i-a) a product of general formula (V) or (IIa) below:

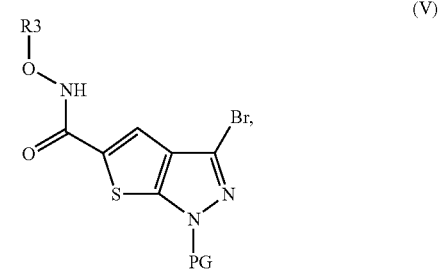
(V)

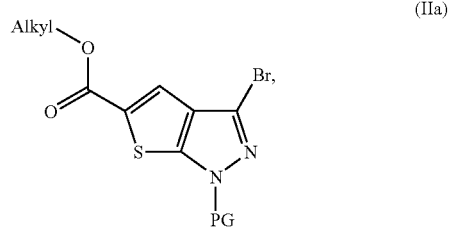
(IIa)

in which R3 and alkyl are as defined above, and in which PG is a protecting group for the free endocyclic NH function of the thieno[2,3-c]pyrazole nucleus, and (i-b) a product of general formula (R2)CONH₂, in the presence of:
a catalyst,
an amine, and
a base, and (ii) cleaving the PG.

20. The process according to claim 19, wherein the catalyst is copper(I) iodide.

21. The process according to claim 19, wherein the amine is selected from trans-1,2-diaminocyclohexane, trans-1,2-bis (methylamino)cyclohexane and N,N'-dimethyl-1,2-diaminoethane.

22. The process as claimed in claim 19, wherein the amine is N,N'-dimethyl-1,2-diaminoethane.

23. The process according to claim 19, wherein the base is selected from tripotassium phosphate and cesium carbonate.

24. A pharmaceutical composition comprising a compound according to claim 1, or a pharmaceutically acceptable salt thereof, in combination with a pharmaceutically acceptable excipient.

25. A pharmaceutical composition comprising a compound according to claim 3, or a pharmaceutically acceptable salt thereof, in combination with a pharmaceutically acceptable excipient.

26. A pharmaceutical composition comprising a compound according to claim 11, or a pharmaceutically acceptable salt thereof, in combination with a pharmaceutically acceptable excipient.

* * * * *

UNITED STATES PATENT AND TRADEMARK OFFICE
CERTIFICATE OF CORRECTION

| | |
|---|---|
| PATENT NO. | : 7,884,123 B2 |
| APPLICATION NO. | : 11/752612 |
| DATED | : February 8, 2011 |
| INVENTOR(S) | : Jean-Christophe Carry et al. |

It is certified that error appears in the above-identified patent and that said Letters Patent is hereby corrected as shown below:

On page 2, in column 2, under "Other Publications", line 17, delete "Synmthetic" and insert -- Synthetic --, therefor.

In column 19, line 31, delete "SN" and insert -- 5N --, therefor.

In column 19, line 47, after "PhO$^+$" insert -- . --.

In column 25, line 31, delete "hemoangioma" and insert -- hemangioma --, therefor.

In column 27, line 31-32, delete "Staurosporin" and insert -- Staurosporine --, therefor.

In column 31, line 44, in claim 1, after "styryl" insert -- ) --.

In column 31, line 45, in claim 1, after "phenoxycarboxamide" insert -- ) --.

In column 33, line 51-52, in claim 18, delete "triakylaluminum" and insert -- trialkylaluminum --, therefor.

Signed and Sealed this
Tenth Day of January, 2012

David J. Kappos
*Director of the United States Patent and Trademark Office*

SEQUENCE LISTING

<160> NUMBER OF SEQ ID NOS: 1

<210> SEQ ID NO 1
<211> LENGTH: 34
<212> TYPE: PRT
<213> ORGANISM: Artificial
<220> FEATURE:
<223> OTHER INFORMATION: Description of Artificial Sequence:
      biotinylated peptide substrate
<220> FEATURE:
<221> NAME/KEY: MISC_FEATURE
<222> LOCATION: (1)..(1)
<223> OTHER INFORMATION: biotinylated
<220> FEATURE:
<221> NAME/KEY: MISC_FEATURE
<222> LOCATION: (34)..(34)
<223> OTHER INFORMATION: hydroxylated

<400> SEQUENCE: 1

Ser Ala Cys Pro Leu Asn Leu Pro Leu Gln Asn Asn His Thr Ala Ala
1               5                   10                  15

Asp Met Tyr Leu Ser Pro Val Arg Ser Pro Lys Lys Lys Gly Ser Thr
            20                  25                  30

Thr Arg